US010842649B2

(12) United States Patent
Rogers et al.

(10) Patent No.: US 10,842,649 B2
(45) Date of Patent: Nov. 24, 2020

(54) SURGICAL OPERATING INSTRUMENT FOR EXPANDABLE AND ADJUSTABLE LORDOSIS INTERBODY FUSION SYSTEMS

(71) Applicant: SpineEX, Inc., Fremont, CA (US)

(72) Inventors: Andrew Rogers, Deephaven, MN (US); Robyn Burrows-Ownbey, Elmdale, KS (US)

(73) Assignee: SpineEX, Inc., Fremont, CA (US)

( * ) Notice: Subject to any disclaimer, the term of this patent is extended or adjusted under 35 U.S.C. 154(b) by 283 days.

(21) Appl. No.: 16/035,637

(22) Filed: Jul. 15, 2018

(65) Prior Publication Data

US 2020/0015985 A1 Jan. 16, 2020

(51) Int. Cl.
*A61F 2/46* (2006.01)
*A61F 2/44* (2006.01)
*A61F 2/30* (2006.01)

(52) U.S. Cl.
CPC .......... *A61F 2/4611* (2013.01); *A61F 2/4455* (2013.01); *A61F 2/4637* (2013.01);
(Continued)

(58) Field of Classification Search
CPC ............ A61F 2/4611; A61F 2002/4625; A61F 2002/4627; A61F 2002/4628; A61B 17/8872
See application file for complete search history.

(56) References Cited

U.S. PATENT DOCUMENTS 4,976,175 A * 12/1990 Hung ..................... B25F 5/029
81/177.5
5,572,905 A * 11/1996 Cook, Jr. .............. B23P 19/069
464/37

(Continued)

OTHER PUBLICATIONS

PCT, International Search Report and Written Opinion of International Searching Authority in PCT/US2018/042199, dated Sep. 27, 2018, 8 pages.

*Primary Examiner* — Anu Ramana
(74) *Attorney, Agent, or Firm* — SpineEX, Inc.

(57) ABSTRACT

An operating instrument includes a housing, a chassis, a first and second drive shaft, a gear assembly, a switch assembly, and a bearing lock assembly. The first and second drive shafts each has a first portion supported by the chassis in the housing and a second portion extending out of the housing. The gear assembly includes a first gear member fixedly received on the first portion of the first drive shaft and a second gear member slidably received on the first portion of the second drive shaft. The switch assembly is operable to place the second gear member into engagement with the first gear member thereby coupling the second drive shaft with the first drive shaft to provide a first operating mode wherein the second drive shaft is rotatable with the first drive shaft, or displace the second gear member out of engagement with the first gear member thereby decoupling the second drive shaft from the first drive shaft to provide a second operating mode wherein the second drive shaft is non-rotatable with the first drive shaft. The bearing lock assembly is operable to lock the first and second drive shafts to the chassis whereby the first and second drive shafts are restricted from sliding out of the housing and are capable of freely rotating or unlock the first and second drive shafts from the chassis to allow the first and second drive shafts to slide out of the housing.

20 Claims, 19 Drawing Sheets

(52) U.S. Cl.
CPC ........... *A61F 2002/30476* (2013.01); *A61F 2002/30523* (2013.01); *A61F 2002/30537* (2013.01); *A61F 2002/30579* (2013.01)

(56) References Cited

U.S. PATENT DOCUMENTS

| | | | |
|---|---|---|---|
| 8,512,348 B2* | 8/2013 | Chabansky | A61F 2/4611 |
| | | | 606/99 |
| 9,572,560 B2* | 2/2017 | Mast | A61B 17/0206 |
| 2002/0116008 A1 | 8/2002 | Lin et al. | |
| 2006/0237205 A1* | 10/2006 | Sia | B25B 23/1405 |
| | | | 173/48 |
| 2007/0167678 A1* | 7/2007 | Moskowitz | A61B 1/07 |
| | | | 600/104 |
| 2008/0319481 A1* | 12/2008 | Moore | A61B 17/15 |
| | | | 606/246 |
| 2011/0064978 A1* | 3/2011 | McGahan | A61B 17/8875 |
| | | | 429/61 |
| 2013/0190575 A1* | 7/2013 | Mast | A61B 17/7079 |
| | | | 600/215 |
| 2015/0066145 A1 | 3/2015 | Rogers et al. | |
| 2015/0112398 A1 | 4/2015 | Morgenstern Lopez et al. | |
| 2015/0202051 A1 | 7/2015 | Tanaka et al. | |
| 2015/0272746 A1 | 10/2015 | Jimenez et al. | |
| 2015/0351925 A1 | 12/2015 | Emerick et al. | |

\* cited by examiner

SURGICAL OPERATING INSTRUMENT FOR EXPANDABLE AND ADJUSTABLE LORDOSIS INTERBODY FUSION SYSTEMS

TECHNICAL FIELD

This disclosure relates generally to surgical procedures and apparatuses for treating spinal diseases. In particular, various embodiments of a surgical insertion and operating instrument for expandable and adjustable lordosis interbody fusion systems are described.

BACKGROUND

Lumbar spinal fusion is a surgical procedure to correct problems relating to the human spine. It generally involves removing damaged disc and bone from between two vertebrae and inserting bone graft material that promotes bone growth. As the bone grows, the two vertebrae join, or fuse, together. Fusing the bones together can help make that particular area of the back more stable and help reduce problems related to nerve irritation at the site of the fusion. Fusions can be done at one or more segments of the spine.

Interbody fusion is a common procedure to remove the nucleus pulposus and/or the annulus fibrosus that compose the intervertebral disc at the point of the back problem and replace it with a cage configured in shape and dimension to restore the distance between adjacent vertebrae to that of a proper condition. Surgical approaches to implement interbody fusion vary, and access to the patient's vertebral column can be made through the abdomen or back. One other surgical method for accomplishing lumbar spinal fusion in a less invasive way involves accessing the vertebral column through a small incision on the side of the body. This procedure is known as lateral lumbar interbody fusion.

Once the intervertebral disc is removed from the body during the lateral lumbar interbody fusion, the surgeon typically forces different trial implants between the vertebral endplates of the specific region to determine the appropriate size of the implant for maintaining a distance between the adjacent vertebrae. Another consideration is to maintain the natural angle between lumbar vertebral bodies to accommodate the lordosis, or natural curvature, of the spine. Therefore, during selection of a cage for implantation, both intervertebral disc height and lordosis must be considered. Prior art fusion cages are often pre-configured to have top and bottom surfaces angles to one another to accommodate the natural curvature of the spine. It is unlikely that these values can be determined precisely prior to the operation, which is a drawback in present procedures. Prepared bone graft is generally packed into the cage implant once it is properly sized and before it is inserted in between the vertebral bodies.

SUMMARY OF THE DISCLOSURE

Embodiments of the disclosure provide a surgical operating instrument for expandable and adjustable lordosis interbody fusion systems. The instrument provides for an improved and more efficient way to connect an interbody fusion implant device and physically implant it into the patient and further expand and lordotically adjust the implant in-situ. The instrument allows for a smoother, more efficient, and more robust operation of an interbody fusion implant once the implant is inserted into the patient. The instrument enables surgeons to expand, lordotically adjust, and position the implant in the patient's intervertebral disc space with a smoother instrument operating interface, while also being able to deliver more force to the instrument if needed without damaging it. The instrument when connected to the implant can be operable and serve as a distraction system where two vertebral bodies can be forced or distracted away from each other. This allows for restoration of the normal intervertebral disc height anatomy for patients with degenerative disc diseases (DDD), deformities, and tumors. This allows for a more streamlined and efficient means for distracting the intervertebral disc space. The instrument's human interface aspects are more intuitive, allowing for a more seamless interaction between the surgeon and the instrument during surgery, ultimately making surgery easier and quicker. The instrument provides for greater ease of assembly and disassembly after surgery to allow the instrument to be cleaned and sterilized so that it can be reused for more surgeries.

An embodiment of a surgical operating instrument includes a housing, a chassis, a first and second drive shaft, a gear assembly, a switch assembly, and a lock or bearing lock assembly. The first and second drive shafts each has a first portion supported by the chassis in the housing and a second portion extending out of the housing. The gear assembly includes a first gear member fixedly received on the first portion of the first drive shaft and a second gear member slidably received on the first portion of the second drive shaft. The switch assembly is operable to place the second gear member into engagement with the first gear member thereby coupling the second drive shaft with the first drive shaft to provide a first operating mode wherein the second drive shaft is rotatable with the first drive shaft, or displace the second gear member out of engagement with the first gear member thereby decoupling the second drive shaft from the first drive shaft to provide a second operating mode wherein the second drive shaft is non-rotatable with the first drive shaft. The bearing lock assembly is operable to lock the first and second drive shafts to the chassis whereby the first and second drive shafts are restricted from sliding out of the housing and are capable of freely rotating or unlock the first and second drive shafts from the chassis to allow the first and second drive shafts to slide out of the housing.

This Summary is provided to introduce selected embodiments in a simplified form and is not intended to identify key features or essential characteristics of the claimed subject matter, nor is it intended to be used as an aid in determining the scope of the claimed subject matter. The selected embodiments are presented merely to provide the reader with a brief summary of certain forms the invention might take and are not intended to limit the scope of the invention. Other aspects and embodiments of the disclosure are described in the section of Detailed Description.

BRIEF DESCRIPTION OF THE DRAWINGS

These and various other features and advantages will become better understood upon reading of the following detailed description in conjunction with the accompanying drawings and the appended claims provided below, where:

DETAILED DESCRIPTION OF EMBODIMENTS

Referring to FIGS. 1-25, various embodiments of a surgical operating instrument will now be described.

Figure 1:
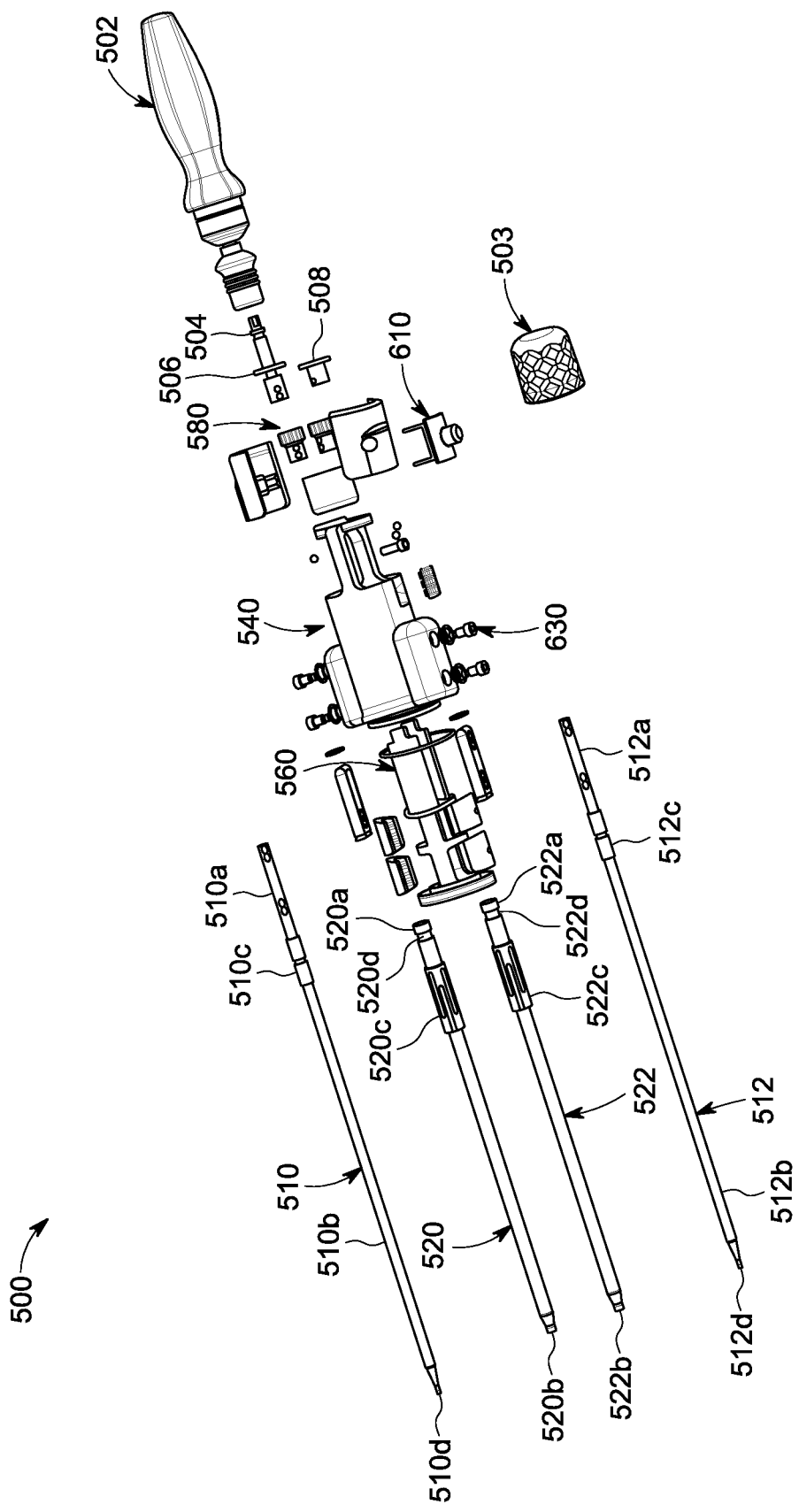
FIG. 1 is an exploded view of an exemplary surgical operating instrument according to embodiments of the disclosure.
Figure 2:
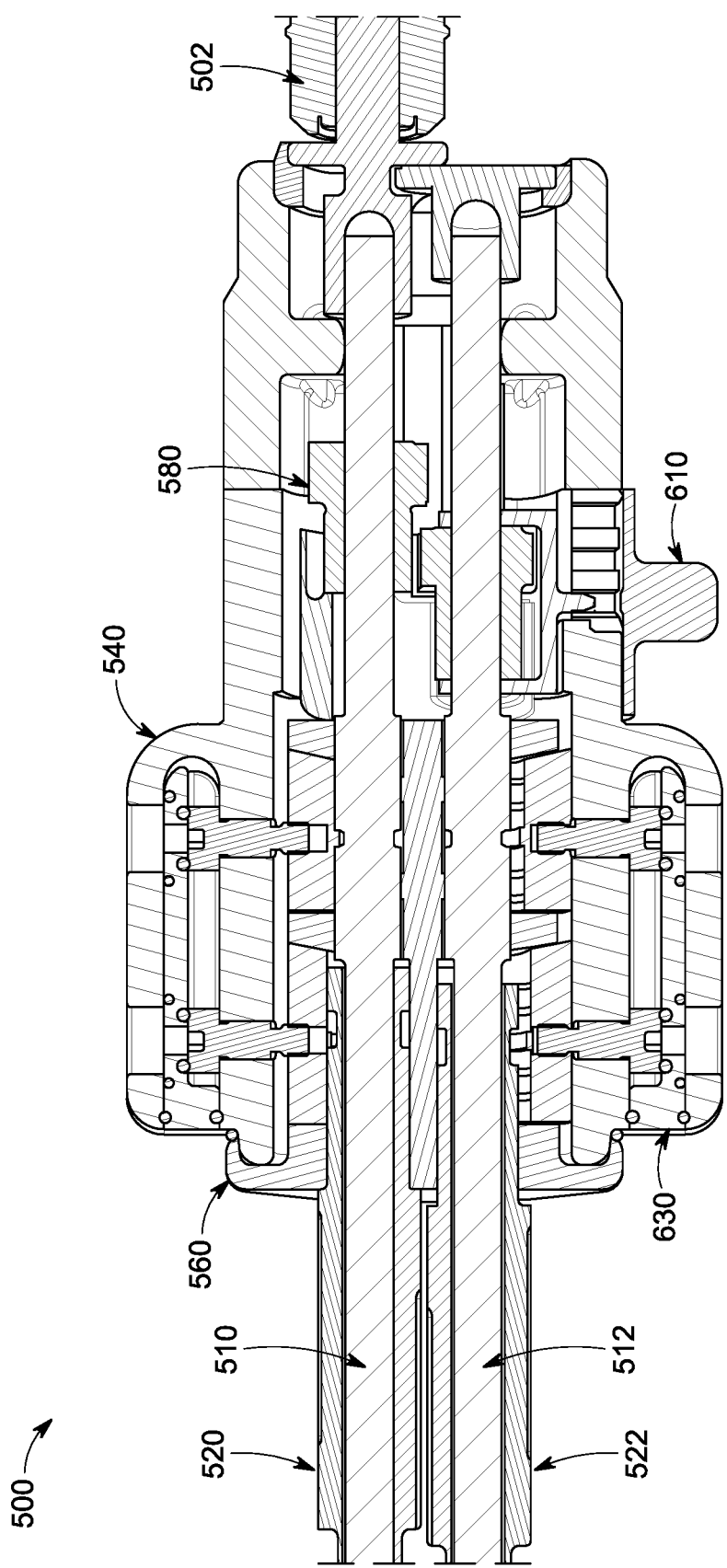
FIG. 2 is a partial, cross-sectional view of an exemplary surgical operating instrument according to embodiments of the disclosure.
Figure 3:
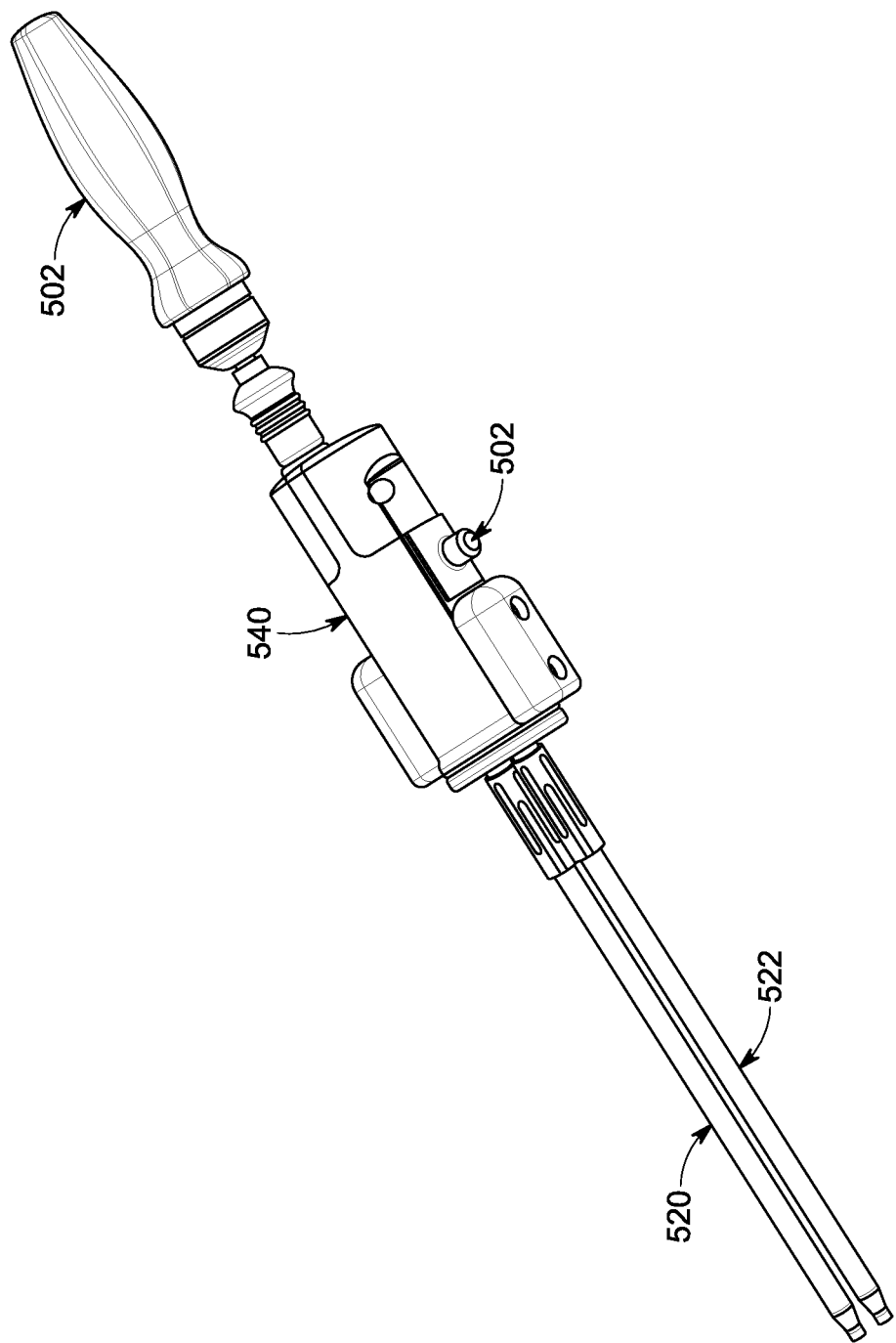
FIG. 3 is a perspective view of an exemplary surgical operating instrument according to embodiments of the disclosure.

FIG. 1 is an exploded view of an exemplary surgical operating instrument 500 according to embodiments of the disclosure. FIG. 2 is a partial, cross-sectional view of the instrument 500. As shown, the instrument 500 in general may include a handle 502, a housing 540, a chassis 560, a pair of drive shafts 510, 512, a pair of sleeves 520, 522, a gear assembly 580, a switch or switch assembly 610, and a lock or bearing lock assembly 630. The handle 502 may be operatively coupled to the pair of drive shafts 510, 512, allowing torque to be applied through the drive shafts to a workpiece such as an interbody fusion device (not shown) to effect expansion, contraction, and/or lordosis adjustment of the fusion device. The pair of sleeves 520, 522, which would surround a portion of the pair of drive shafts 510, 512 outside the housing 540, serve to connect the instrument 500 to a workpiece such as an interbody fusion device. The housing 540 encloses and protects the gear assembly 580, the bearing lock assembly 630, a portion of the drive shafts 510, 512 and sleeves 520, 522, and other components supported by the chassis 560. The chassis 560 serves as a foundation of the instrument 500, providing support for the drive shafts 510, 512, the sleeves 520, 522, and the housing 540. The chassis 560 may also serve as a partial housing for the gear assembly 580 and other components. The switch assembly 610, in conjunction with the gear assembly 580, operates to provide various operating modes of the instrument 500. The bearing lock assembly 630 operates to lock or unlock the drive shafts 510, 512 and sleeves 520, 522 to or from the chassis 560 inside the housing 540. FIG. 3 is a perspective view of the instrument 500 assembled according to embodiments of the disclosure.

Referring to FIGS. 1 and 2, the handle 502 may be any suitable handle that the user can apply torque to the drive shafts 510, 512. The handle 502 can be driven manually or by a motor or robotics. The handle 502 can be shaped in various configurations including I-shaped or T-shaped configurations. The handle 502 may be a bi-directional ratchet handle which can apply torque by rotating both clockwise and counterclockwise. The handle 502 may be a torque limiting ratchet handle which can limit the torque applied by the user so that damage to a workpiece does not take place. In some embodiments, the workpiece is an interbody fusion device and the handle 502 is a bi-directional torque limiting ratchet handle to effect expansion, contraction, lordosis, kyphosis, and/or coronal adjustment of the device. Torque limiting ratchet handles are commercially available for example from Bradshaw Medical, Inc. in Kenosha, Wis.

Figure 4:
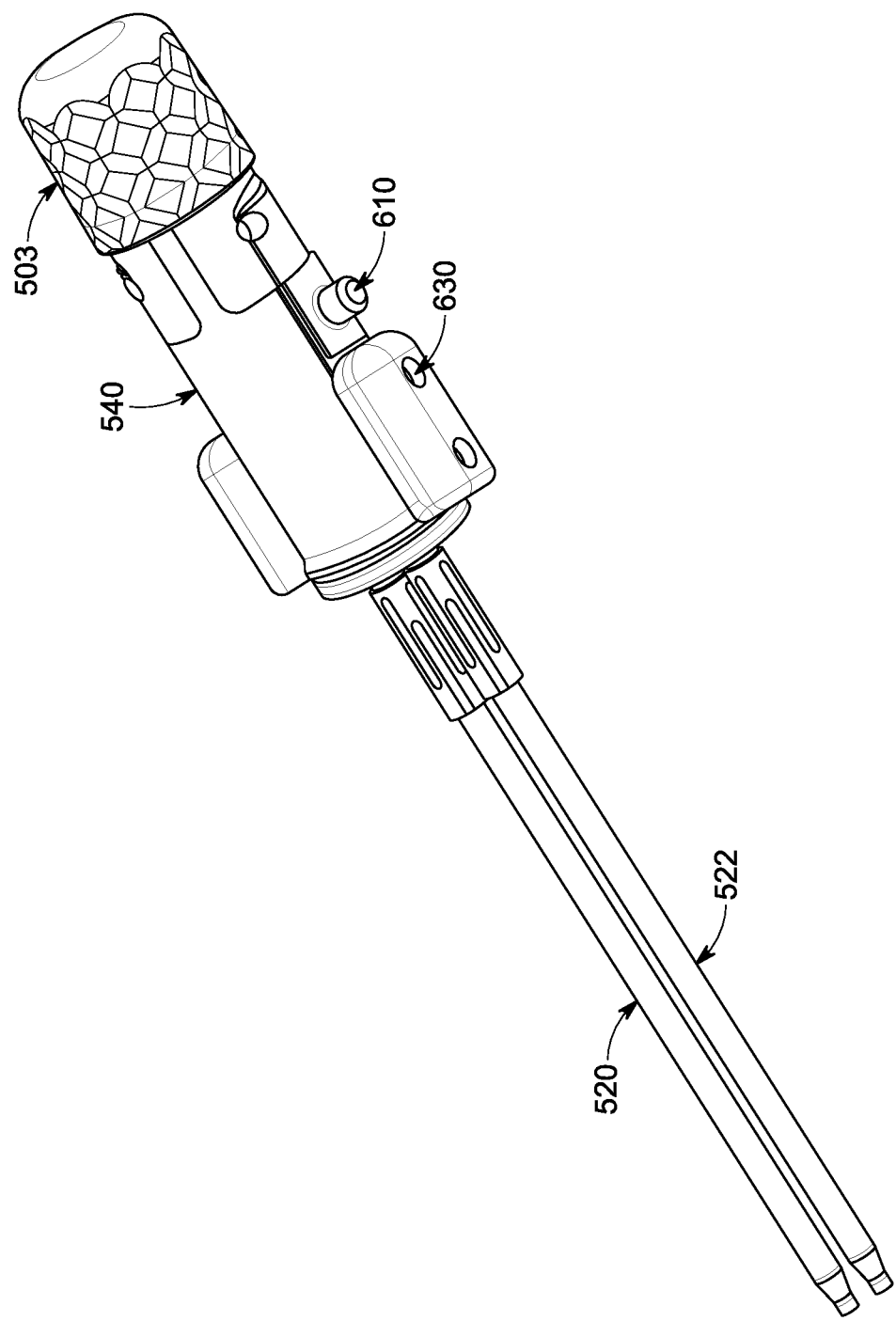
FIG. 4 is a perspective view of an exemplary surgical operating instrument according to embodiments of the disclosure.

The handle 502 can be removed and replaced with an impact cap 503. FIG. 4 is a perspective view of an exemplary operating instrument 500 including an impact cap 503 according to embodiments of the disclosure. The impact cap 503 can be made of stainless steel, allowing the user to exert a forward force through the instrument by striking the impact cap with e.g. a mallet. This feature of the instrument can help push or wedge e.g. an interbody fusion device into the patient's vertebral space with more ease. The impact cap 503 can avoid or reduce damages to the instrument when a hammering force is applied during the surgery.

Figure 23:
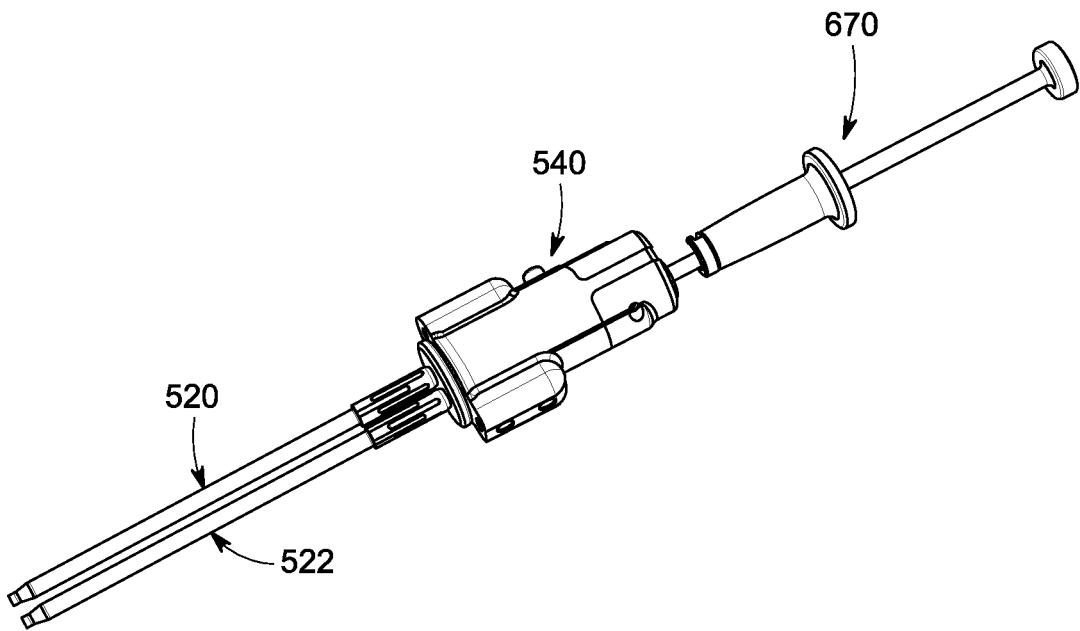
FIG. 23 is an isometric view of an exemplary surgical operating instrument including a slap hammer according to embodiments of the disclosure.
Figure 24:
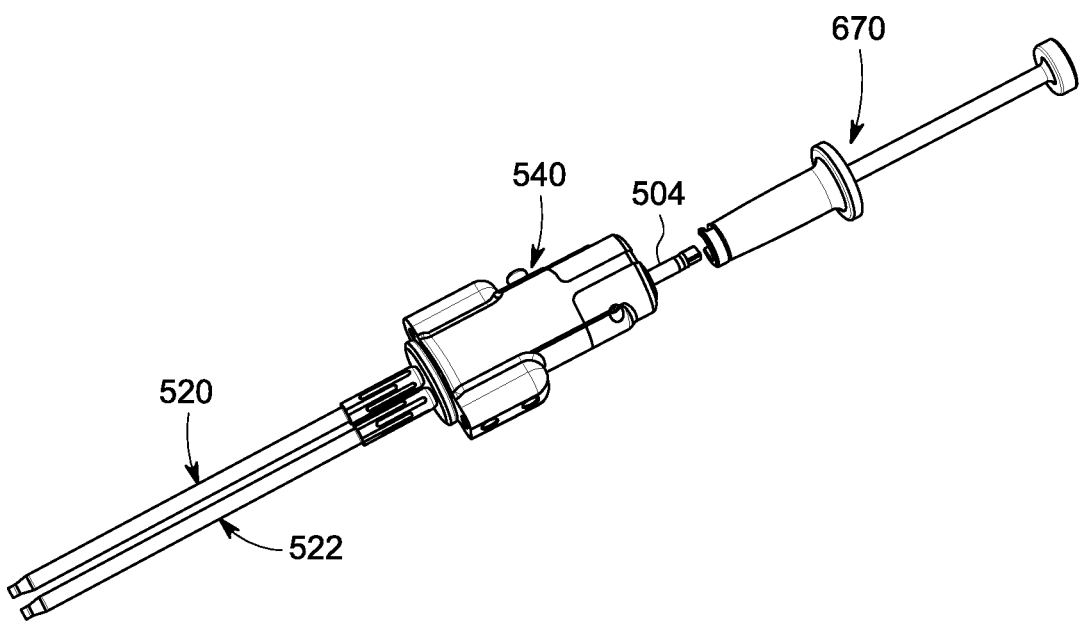
FIG. 24 is an isometric exploded view of the exemplary surgical operating instrument shown in FIG. 23 according to embodiments of the disclosure.
Figure 25:
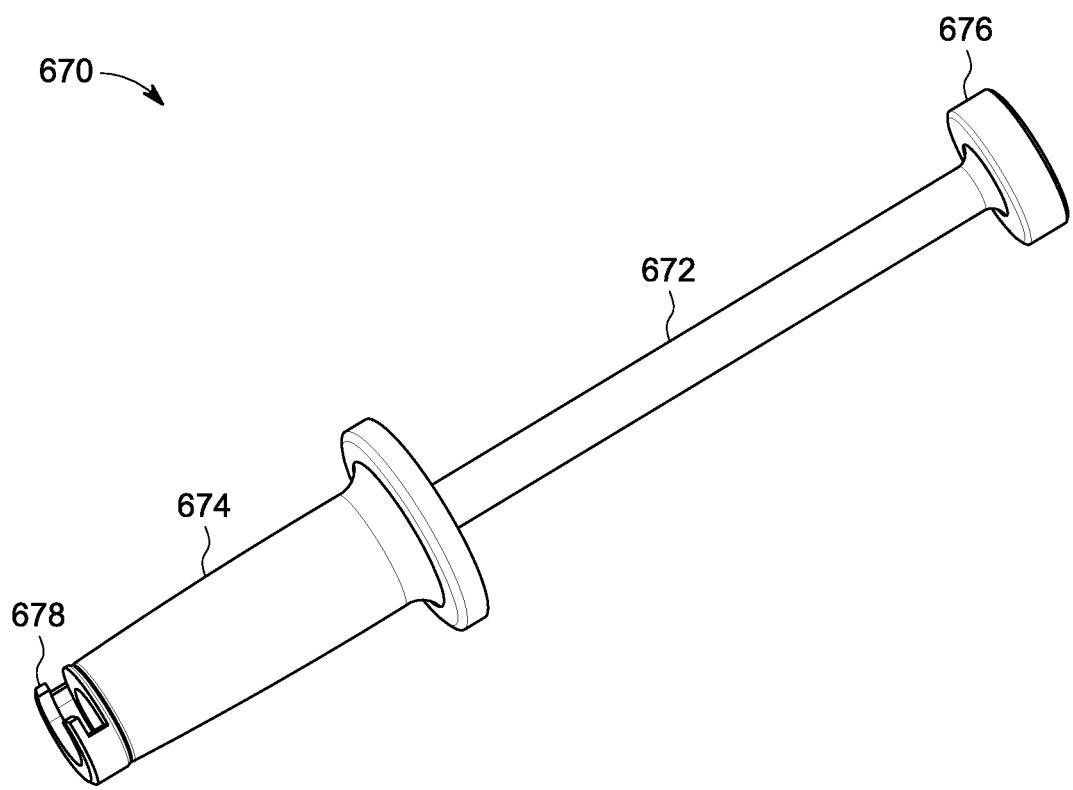
FIG. 25 is an isometric view of an exemplary slap hammer according to embodiments of the disclosure.

In some embodiments, the handle 502 or the impact cap 503 may be removed and replaced with a slap hammer. A slap hammer can aid in providing a pull or removal force to the instrument 500 and the interbody fusion device if the surgeon desires to remove the implant following expansion and adjustment of the device or potentially even partial fusion of the device in a secondary removal surgery. FIG. 23 is an isometric view of an exemplary surgical operating instrument including a slap hammer 670 according to embodiments of the disclosure. FIG. 24 is an isometric exploded view of the exemplary surgical operating instrument shown in FIG. 23. FIG. 25 is an isometric view of an exemplary slap hammer according to embodiments of the disclosure. As shown, the slap hammer 670 may include an elongate bar 672 and a hammer weight 674. The hammer weight 674 is configured to be gripped by the user and can slide along the elongate bar 672 when a force is applied. At the first or proximal end of the elongate bar 672, a stopper 676 may be provided to prevent the hammer weight 674 from coming off the elongate bar 672. The stopper 676 may be removably coupled to the bar 672 via e.g. a threaded connection. At the second or distal end of the elongate bar 672, a connection site 678 may be provided to couple the slap hammer 670 with the instrument 500. By way of example, the connection site 678 may be configured such that the slap hammer 670 can be coupled to the adapter 504 of the instrument 500 via a threaded connection, a clip-on connection, slotted "key-like" connection, or the like.

Referring to FIGS. 1-2, the housing 540 encloses the gear assembly 580, the chassis 560, the bearing lock assembly 630, a portion of the drive shafts 510, 512 and sleeves 520, 522 etc., protects the components from contamination by biomaterials, and/or prevents outside objects from obstructing or interfering with the component operation. The housing 540 may be constructed of a material that can withstand high sterilization steam temperatures at many cycles and/or of a material that provides mechanical strength to the instrument. Suitable materials for constructing the housing 540 include stainless steel, medical grade plastics such as Rader) R5500 Polyphenylsulfone (PPSU), which is commercially available from Solvay Advanced Polymers of Brussels, Belgium. The housing 540 can be shaped to give an aesthetic appeal, and/or shaped ergonomically for the user to grip the instrument.

Figure 5:
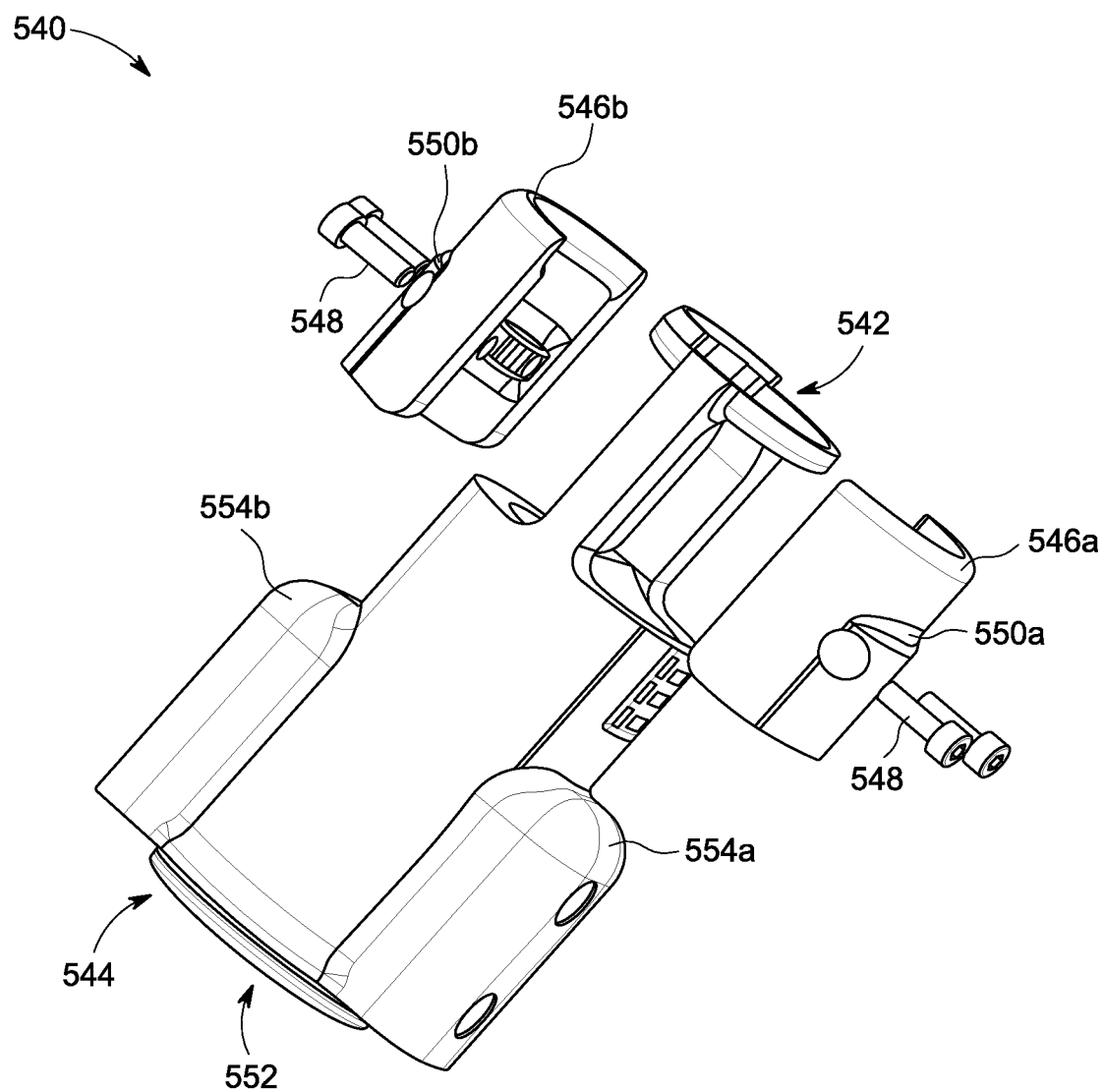
FIG. 5 is an exploded view of a housing including housing covers according to embodiments of the disclosure.
Figure 6:
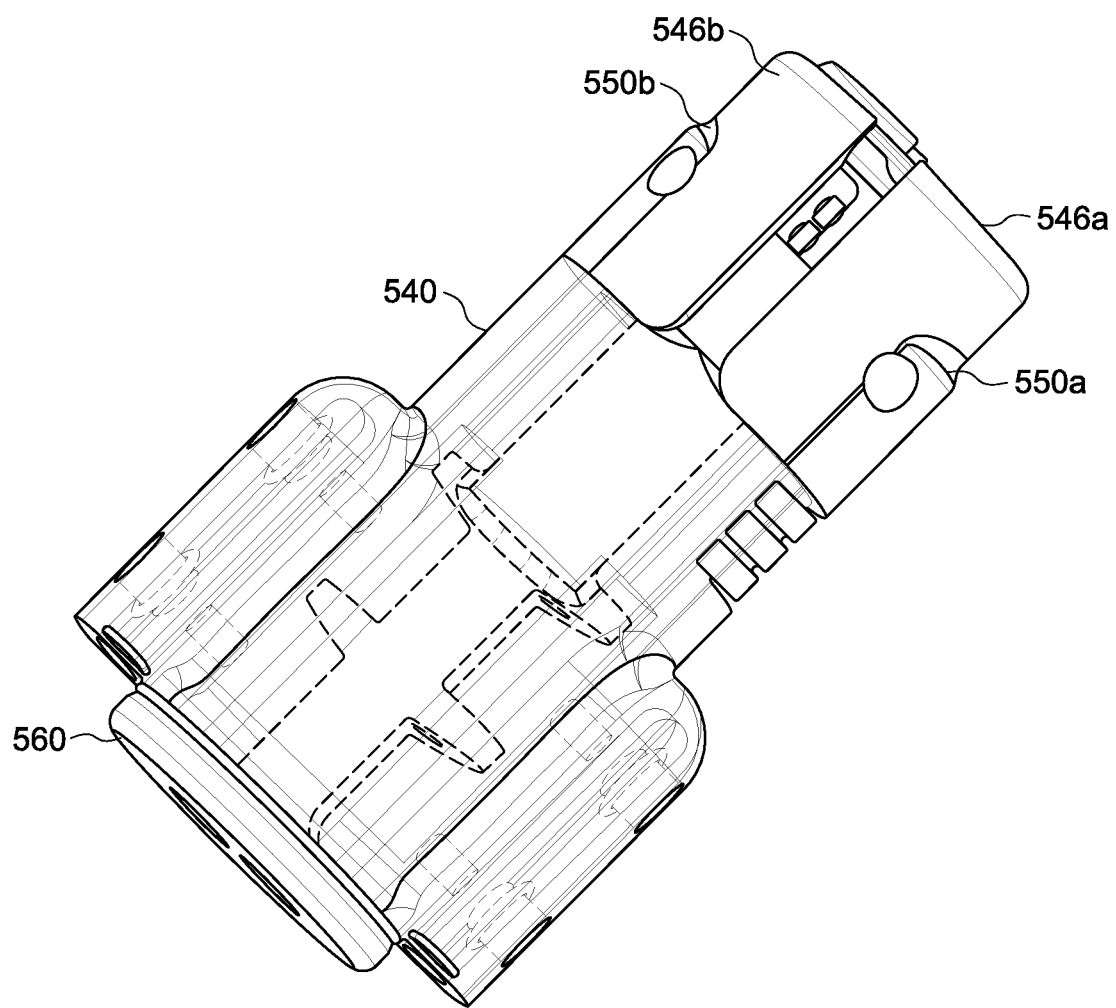
FIG. 6 schematically shows a housing enclosing a chassis according to embodiments of the disclosure.

Referring to FIG. 5, the housing 540 may include a first end portion 542 proximal to the handle 502 and a second end portion 544 distal to the handle 502. In the first end portion 542, the housing 540 may include two housing covers 546a, 546b. The housing covers 546a, 546b may be separate pieces secured to the chassis 560 with e.g. screws 548, bolts, or the like. The housing covers 546a, 546b can be disattached from the chassis 560 during cleaning and sterilization to help clean the instrument more efficiently and allow for the inside of the instrument to dry quicker following the sterilization. The removable housing covers 546a, 546b allow for exposure of the gear assembly, the gear lock and other components inside of the chassis or housing, which in turn allows for quick and more efficient drying following sterilization. The housing covers 546a, 546b can be constructed of a medical grade plastic or a metal such as stainless steel to add mechanical strength to the instrument. In some embodiments, the housing covers 546a, 546b each may be configured to provide a shoulder 550a, 550b for an impact cap 503 to sit on (FIGS. 1 and 4). As described above, in some situations it would be desirable to exert a forward force through the instrument to help push or wedge e.g. an interbody fusion device into the patient's vertebral space. By removing the handle 502 from the instrument and placing an impact cap 503 on, the user may exert a forward force through the instrument by striking the impact cap using e.g. a mallet. Because the impact cap 503 would sit on the shoulders 550a, 550b of the housing 540 and not be coupled to the drive shafts 510, 512 or other functional components, a hammering force applied on the impact cap 503 would allow for the force to be equally distributed throughout the cross-sectional area of the body of the instrument and would further not damage the instrument. FIG. 6 shows the housing 540 enclosing the chassis 560, with the housing covers 546a, 546b attached to the chassis 560 providing shoulders 550a, 550b to allow an impact cap to sit on.

Figure 7:
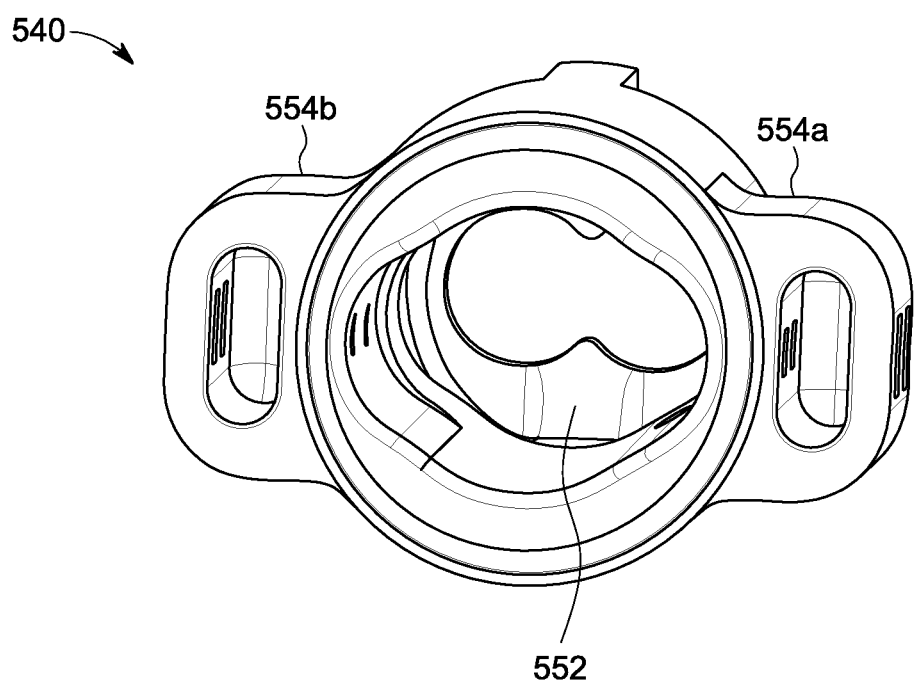
FIG. 7 is a perspective end view of a housing according to embodiments of the disclosure.
Figure 8:
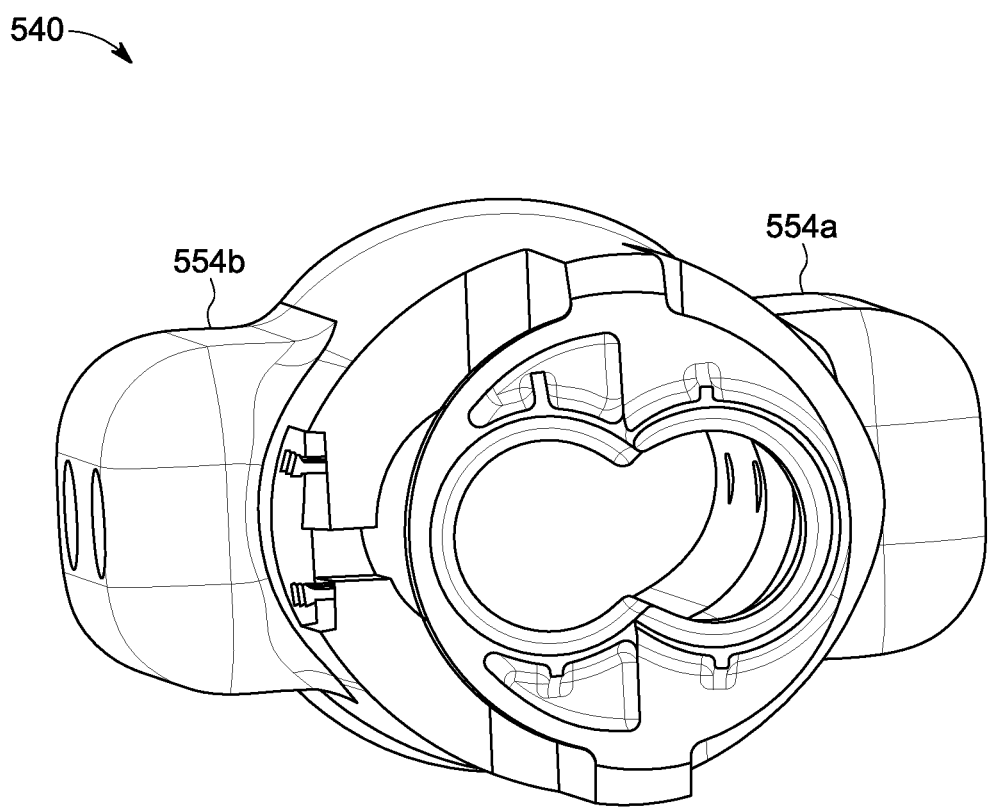
FIG. 8 is a perspective front view of a housing according to embodiments of the disclosure.
Figure 11:
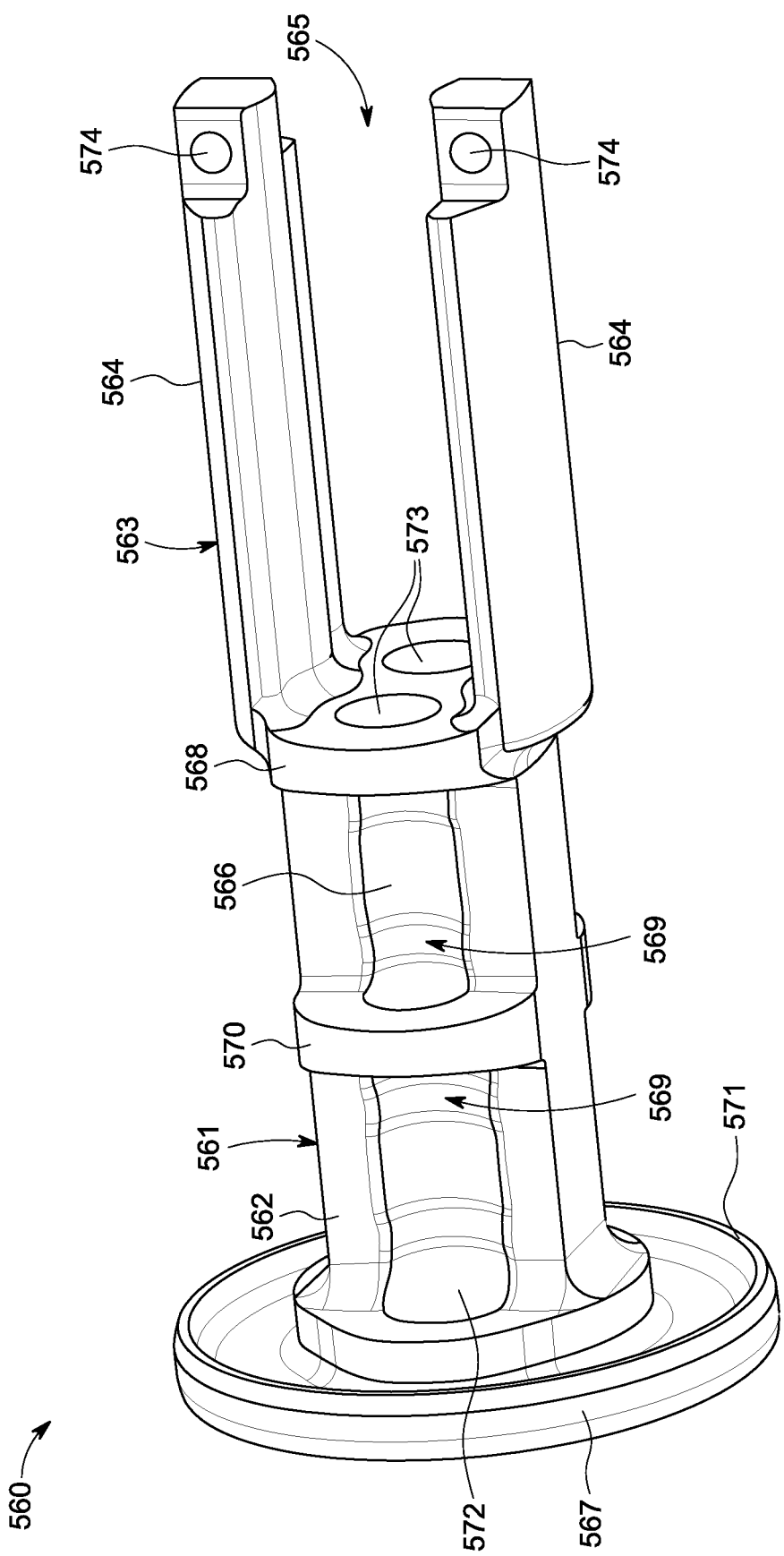
FIG. 11 is a perspective view of an exemplary chassis according to embodiments of the disclosure.

In the second end portion 544 of the housing 540, the housing 540 is provided with an opening 552 configured to allow a main portion of the chassis 560 to be placed inside. The housing 540 may sit on the bottom base 567 of the chassis 560, which may include a raised rim 571 to surround the distal end of the housing 560 (FIG. 11). Threading may be provided on the distal end of the housing 560 for connecting to the chassis 560. Gaskets may be used to provide tight fit and sealing to prevent biomaterials and water from entering into the housing. Two sub-housings or chambers 554a, 554b may be provided at the second end portion for housing the bearing lock assembly 630 to be described in greater detail below. The sub-housings 554a, 554b may be integrally formed with the main body of the housing and arranged opposite to one another. The sub-housings 554a, 554b may be configured to allow retaining plates 652, 654 of the bearing lock assembly 630 (FIG. 22), to be described below, to be inserted inside through a press fit and taken out easily for cleaning and sterilization. Apertures may be provided in the side walls of the sub-housings 554a, 554b to allow access of a torque-applying tool to fasteners and connection of the fasteners to bearings of the bearing lock assembly 630, to be described in greater detail below. FIG. 7 is a perspective end view of the housing 540 showing an opening 552 configured to receive the chassis and sub-housings 554a, 554b for a bearing lock assembly 630. FIG. 8 is a perspective front view of the housing 540.

Figure 9:
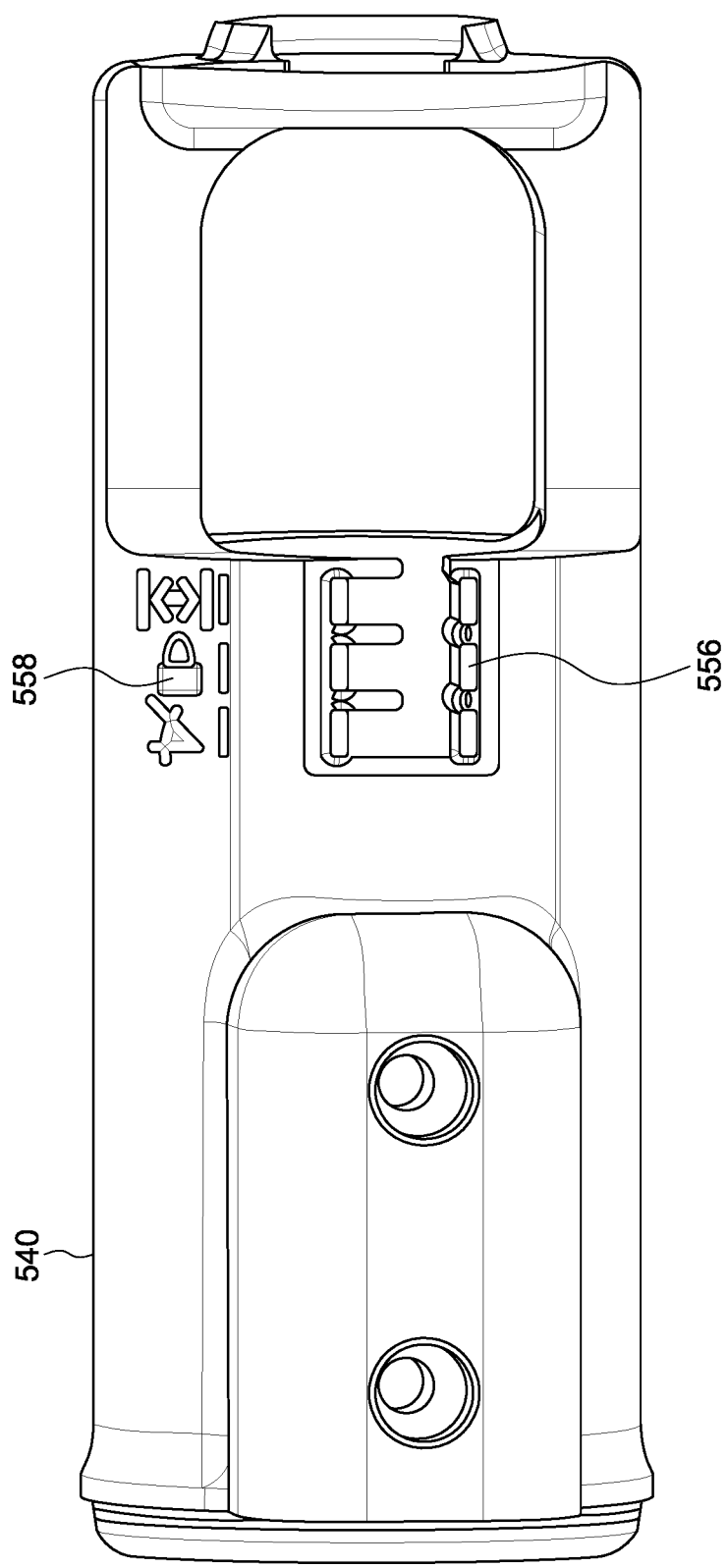
FIG. 9 is a perspective side view of a housing showing switch guide features according to embodiments of the disclosure.
Figure 10:
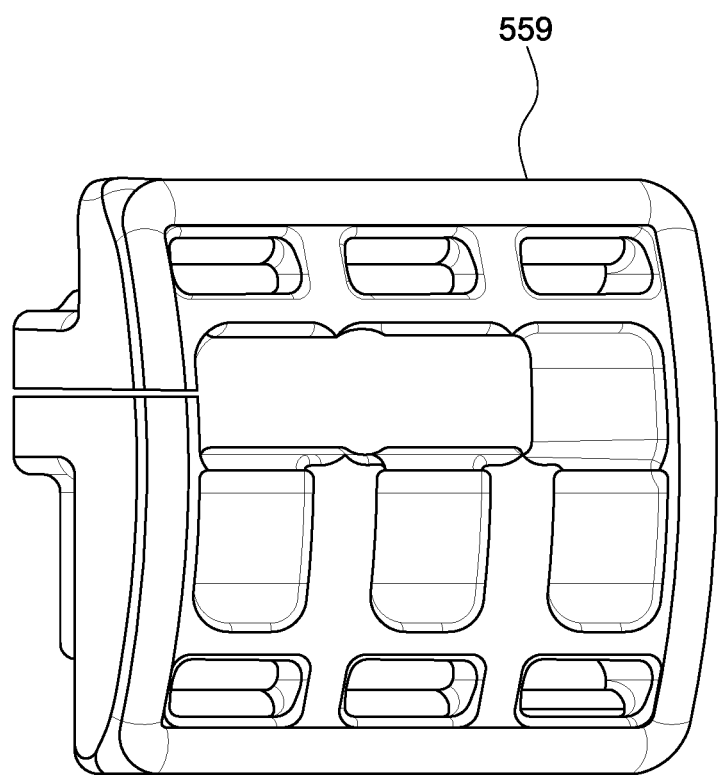
FIG. 10 is a perspective view of a switch gasket according to embodiments of the disclosure.

Referring to FIG. 9, the housing 540 may include a switch guide track 556 for guiding the user in operating the instrument with the switch or switch assembly 610. The guide track 556 may include slots corresponding to different operating modes or settings when the switch is placed in. Indicia 558 may be provided next to the guide track 556 to indicate the various operating settings. In some embodiments, a gasket 559 (FIG. 10) may be coupled to the guide track 556 to allow the user to more smoothly and seamlessly operate the switch. The gasket 559 may also help to keep biomaterials out of the inside of the housing through the switch site. FIG. 10 schematically shows an exemplary gasket 559. The gasket 559 may fit over hooks in the guide track 556 by tension or by other suitable means. The gasket 559 may be made of an elastic material such as silicone rubber. A silicone rubber material allows the gasket to withstand high sterilization temperatures without melting or deforming.

Referring to FIGS. 1-2, the chassis 560 serves as a main foundation of the operating instrument 500. The chassis 560 provides support for the drive shafts 510, 512, the sleeves 520, 522, and the housing 540. The upper part of the chassis 560 may also serve as a partial housing for the gear assembly 580 and other components and provide a secure point for the housing covers 546a, 546b. The chassis 560 may be constructed of a metal such as stainless steel or a medical grade plastic such as Rader) R5500 Polyphenylsulfone (PPSU), providing for a rugged operating instrument so that in case the instrument is dropped on the floor it does not break. The chassis 560, in conjunction with the housing 540 and the impact cap 503, allows for the user to apply a hammering force to the instrument without damaging it. Inclusion of the chassis 560 in the instrument 500 simplifies assembling, disassembling, and cleaning of the instrument.

FIG. 11 schematically shows an exemplary chassis 560 according to embodiments of the disclosure. As shown, the chassis 560 may in general include a first or lower portion 561 and a second or upper portion 563. The lower portion 561 may include a main body 562 providing support for the drive shafts 510, 512 and sleeves 520, 522. The upper portion 563 may include spaced-apart arms 564 defining a partial housing 565 for the gear assembly 580, gear lock 592, and switch assembly 610, to be described in greater detail below.

Figure 12:
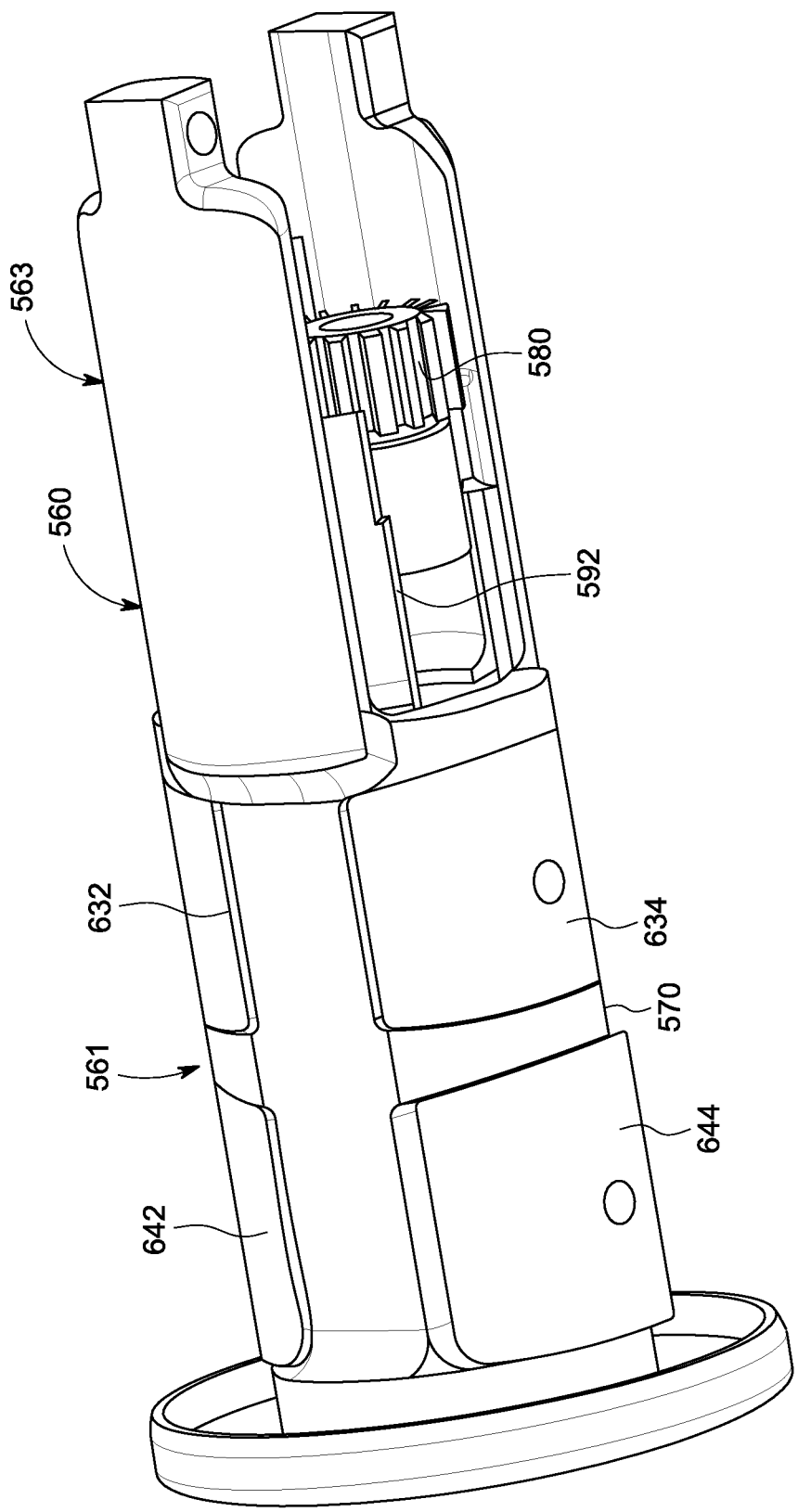
FIG. 12 is a perspective view of an exemplary chassis with sleeve and drive shaft bearings and other components being placed on the chassis according to embodiments of the disclosure.
Figure 13:
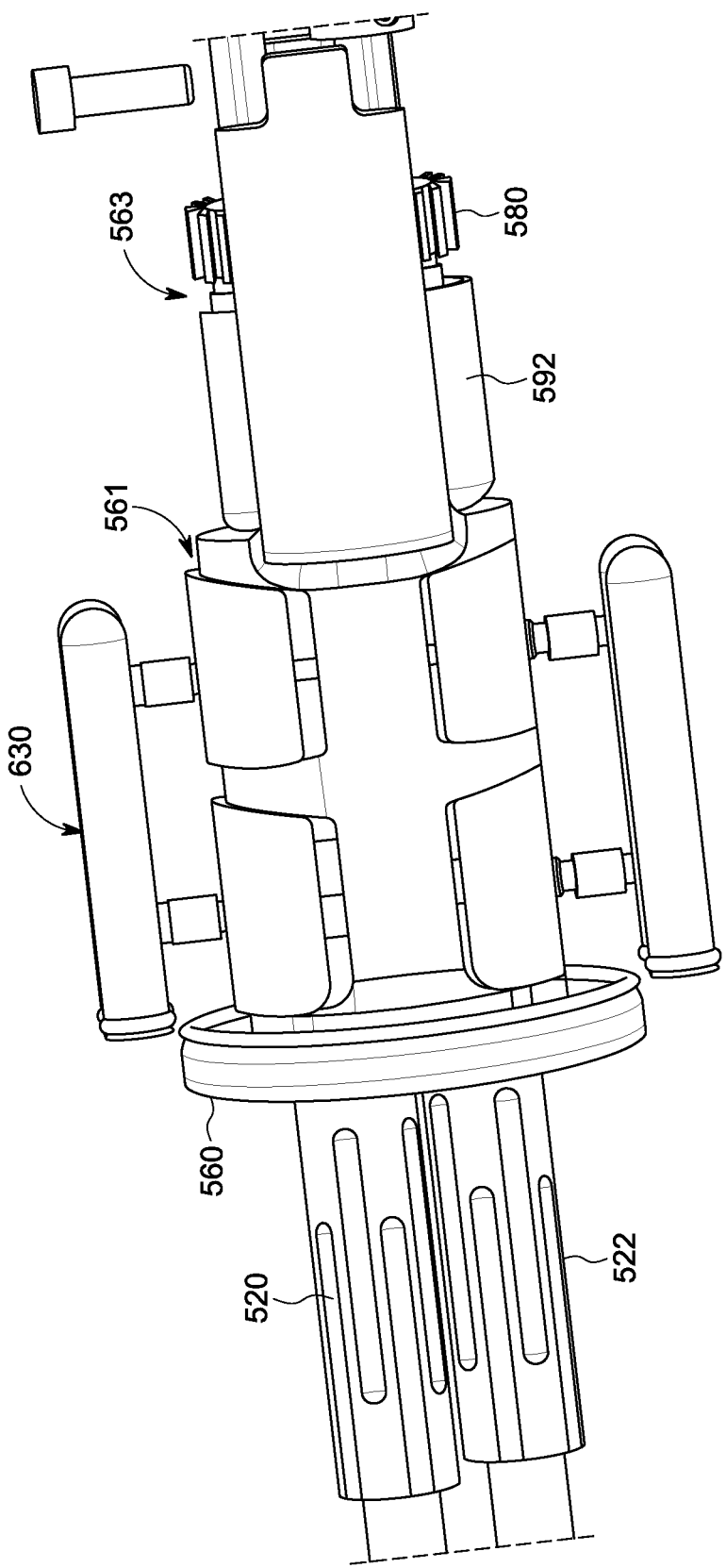
FIG. 13 is a partial perspective view showing an exemplary chassis, a bearing lock assembly, and other components according to embodiments of the disclosure.

In the lower portion 561 of the chassis 560, the main body 562 may be provided with a pair of elongate channels 566 extending between a bottom base 567 and an upper base 568. The pair of elongate channels 566 may be provided in parallel to one another along the opposite sides of the main body 562. The channels 566 may be configured e.g. to have a generally arcuate surface to allow the generally cylindrical drive shafts or sleeves to fit in and spin. A plurality of ridges 569 may be provided on the channel surfaces to keep the drive shafts and sleeves tight against the chassis when fastened by a bearing lock assembly 630, to be described in greater detail below. The ridges 569 on the channel surfaces may keep the drive shafts and sleeves pressed tight against the chassis body 562 when fastened to restrict the drive shafts and sleeves from free movement in the axial direction. A divider 570 may be provided to divide the channels 566 into two sections. The divider 570 allows for separate bearings to lock the draft shafts and sleeves to the chassis independently each other. For example, drive shaft bearings 632, 634 may lock the drive shafts 510, 512 to the chassis 560 at the upper section of the channels 566 whereas sleeve bearings 642, 644 may secure the sleeves 520, 522 to the chassis 560 at the lower section of the channels 566 (FIGS. 12 and 13). The divider 570 can keep the drive shaft bearings 632, 634 and sleeve bearings 642, 644 separate from each other and allow the bearings to rest on the chassis 560 as a support structure during assembly and operation. The bottom base 567 has a raised rim 571 to allow the housing 540 to rest on the chassis 560. Openings 572 provided in the bottom base 567 allow the drive shafts 510, 512 and sleeves 520, 522 to pass through and fit into the channels 566 on the chassis 560 respectively. The upper base 568 is provided with openings 573, allowing the drive shafts 510, 512 to pass through and extend into the partial housing 565 defined by the spaced-apart arms 564. The upper base 568 may also provide support for the gear assembly 580 and the gear lock 592 while adding strength to the chassis or the operating instrument.

In the upper portion 563 of the chassis 560, the spaced-apart arms 564 define a partial housing 565 for the gear assembly 580, the gear lock 592, and the switch assembly 610. The arms 564 may also be configured to secure the gear lock 592, to be described in greater detail below. For example, the arms 564 may be configured to have an internal surface contour that mates with an outer surface contour of the gear lock 592. By way of example, the arms 564 may have convex inner surface portions that mate with concave outer surface portions of the gear lock 592 so that when the gear lock 592 is flexed and/or slid into the partial housing 565 and sits on the upper base 568, the gear lock 592 is secured and would not turn when torque is applied. Alternatively, the arms 564 may have concave inner surface portions that mate with convex outer surface portions of the gear lock 592. The arms 564 may be provided with features such as holes 574 with internal threads for securing housing covers 546a, 546b to the chassis 560 (FIGS. 5 and 6).

FIG. 12 a is perspective view showing a chassis 560 with drive shaft bearings 632, 634 and sleeve bearings 642, 644 being placed on the main body 562 in the lower portion 561, and with the gear lock 592 and gear assembly 580 being accommodated in the partial housing 565 in the upper portion 563. FIG. 13 is a partial perspective view showing a chassis 560 with a gear lock 592 and gear assembly 580 being accommodated in partial housing in the upper portion 563 and a pair of drive shafts 510, 512 (not shown in FIG. 12) and sleeves 520, 522 being secured by a bearing lock assembly 630 on the main body 562 in the lower portion 561. In FIG. 13, the housing 560 is removed to more clearly show the positional relationship between the chassis 560 and the bearing lock assembly 630, to be described in greater detail below.

Referring to FIGS. 1 and 2, the pair of drive shafts 510, 512 are operably coupled to the handle 502 to apply torque to a workpiece (not shown). The pair of drive shafts 510, 512 may include a first drive shaft 510 and a second drive shaft 512. The first drive shaft 510 may be operably connected with the handle 502 e.g. via an adapter 504. The second drive shaft 512 may be coupled with the first drive shaft 510 or decoupled from the first drive shaft 510 via the gear assembly 580. When the second drive shaft 512 is operably coupled with the first drive shaft 510, a first operating mode is provided wherein the handle 502 can rotate both the first drive shaft 510 and the second drive shaft 512. When the second drive shaft 512 is decoupled from the first drive shaft 510, a second operating mode is provided wherein the handle 502 rotates solely the first drive shaft 510.

The pair of drive shafts 510, 512 may be rotatably secured to the chassis 560 in the housing 540 by a bearing lock assembly 630 to be described in greater detail below. The pair of drive shafts 510, 512 may each include a first portion 510a, 512a received in the housing 540 when assembled, and a second portion 510b, 512b extending out of the housing 540. The first portions 510a, 512a of the pair of drive shafts 510, 512 may be configured to be received in the pair of elongate channels 566 of the chassis 560 and rotatably secured to the chassis 560. For example, the first portions 510a, 512a of the pair of drive shafts 510, 512 may include a section of increased diameter and a groove 510c, 512c providing space for a bearing notch to fit in or flush against, thereby restricting the drive shafts 510, 512 from sliding out of the housing 540 while allowing them to freely rotate. The first portions 510a, 512a of the pair of drive shafts 510, 512 may extend into the partial housing 565 of the chassis 560 to receive a gear member, a dial, or an adapter. For example, the first portions 510a, 512a may include a flattened surface and a remaining cylindrical surface at the proximal end configured to receive a gear member, an adapter, or a dial, which may be provided with a channel, cutout, or aperture having a corresponding flattened surface and cylindrical surface. When a gear member, an adapter, or a dial is received on the first portions 510a, 512a, the flattened surfaces prevent rotational movement of the gear member, adapter, or dial relative to the drive shafts 510, 512 when secured with a set screw or the like. The pair of drive shafts 510, 512 may have a substantially same length and cross-sectional geometry along the length. Alternatively, the pair of drive shafts 510, 512 may have different lengths and cross-sectional geometries. For example, the first drive shaft 510 may extend its length and connect with the handle 502 directly without the need for an adaptor.

The second portions 510b, 512b of the drive shafts 510, 512 include a tip 510d, 512d having features configured to engage a workpiece. The workpiece-engaging tip may have a torx or hexalobular, or modified torx or hexalobular configuration. Other suitable configurations or features known in the art may also be used to engage a workpiece having corresponding engaging features. The workpiece may be an interbody fusion implant device described U.S. Pat. No. 9,889,019, the disclosure of all of which is incorporated herein by reference in its entirety. The workpiece may also be other medical devices operable to expand, contract, or tilt by use of an operating instrument.

Referring to FIGS. 1-2, the pair of sleeves or tubular shafts 520, 522 operate to connect the operating instrument 500 to a workpiece such as an interbody fusion implant device. The pair of sleeves 520, 522 may include a first sleeve 520 surrounding the second portion 510b of the first drive shaft 510 extending out of the housing 540, and a second sleeve 522 surrounding the second portion 512b of the second drive shaft 512 extending out of the housing 540. The pair of sleeves 520, 522 may be rotatably secured to the chassis 560 via the bearing lock assembly 630, to be described below, so that the sleeves 520, 522 can freely spin or rotate independently of the rotation of the pair of drive shafts 510, 512, and are restricted from sliding out of the housing 540 during operation but may be removed following operation for cleaning and sterilization purposes.

The pair of sleeves 520, 522 may be generally cylindrically shaped having an inner diameter greater than an outer diameter of the second portions 510b, 512b of the drive shafts 510, 512. The sleeves 520, 522 may each include a first end portion 520a, 522a configured to be rotatably secured to the chassis 560 in the housing 540 and a second end portion 520b, 522b having features configured to connect with a workpiece. A finger grip 520c, 522c may be provided on each of the sleeves 520, 522 to facilitate rotating or spinning of the sleeves in connecting with a workpiece. The first end portions 520a, 522a of the pair of sleeves 520, 522 may be configured to be received in the elongate channels 566 of the chassis 560 and rotatably secured to the chassis. The first end portions 520a, 522a of the pair of sleeves 520, 522 may each include a groove 520d, 522d providing space for a bearing notch to fit in or flush against, thereby restricting the sleeves 520, 522 from sliding out of the housing 540 while allowing the sleeves 520, 522 to freely rotate. The second end portion 520b, 522b of the sleeves 520, 522 may be provided with internal threads or other suitable features configured to connect with a workpiece such as a spinal implant device having corresponding connecting features such as external threads.

Referring to FIGS. 1 and 2, the gear assembly 580 serves to couple the second drive shaft 512 with the first drive shaft 510 or decouple the second drive shaft 512 from the first drive shaft 510, providing various operating modes. In some embodiments, the gear assembly 580 may lock the second and first drive shafts 510, 512 so that rotation of the first and second drive shafts 510, 512 are prohibited.

Figure 18:
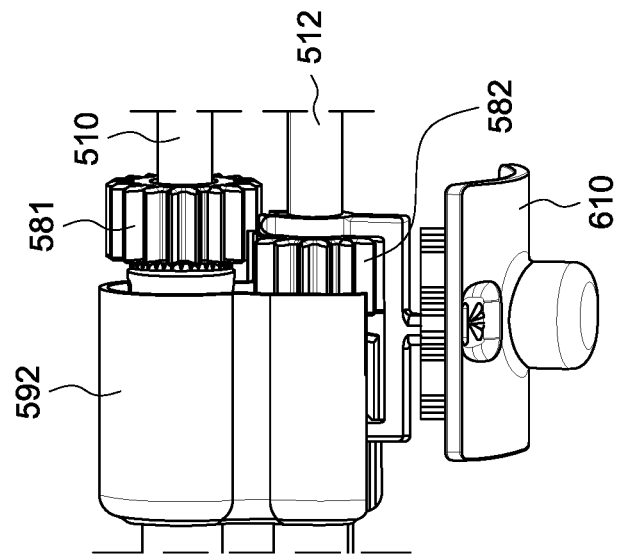
FIG. 18 is a partial perspective view showing a gear assembly and a switch assembly in a third operating setting according to embodiments of the disclosure.
Figure 17:
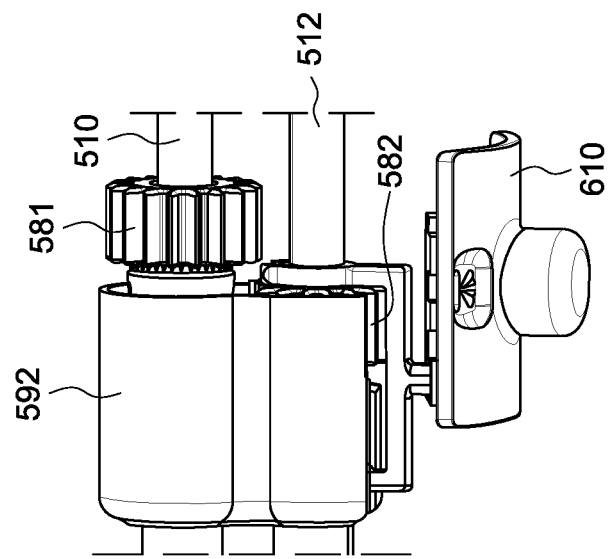
FIG. 17 is a partial perspective view showing a gear assembly and a switch assembly in a second operating setting according to embodiments of the disclosure.
Figure 16:
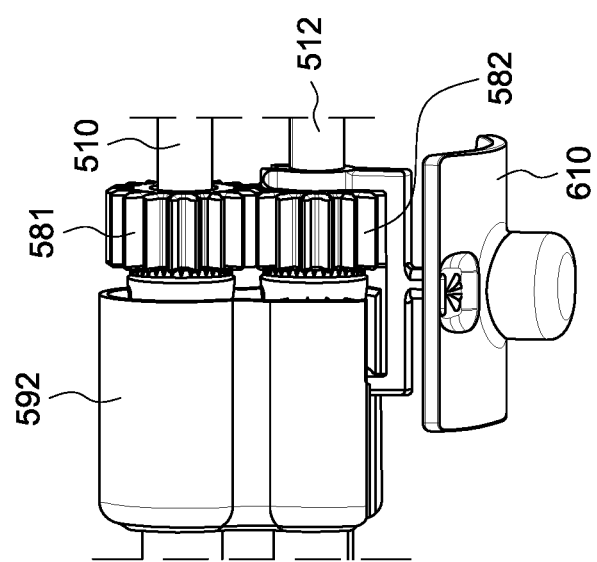
FIG. 16 is a partial perspective view showing a gear assembly and a switch assembly in a first operating setting according to embodiments of the disclosure.

The gear assembly 580 may include a pair of spur gears having substantially parallel gear axes. A first gear member 581 may be received on the first drive shaft 510 and a second gear member 582 may be received on the second drive shaft 512 (FIGS. 16-18). The first gear member 581 may be fixedly secured to the first drive shaft 510 via screws, keys, pins or the like. The second gear member 582 may be slidably received on the second driving shaft 512 but secured from rotating relative to the second drive shaft via set screws, keys, pins, or the like. A toggle switch 610, to be described in greater detail below, may be received and slidably move on the second driving shaft 512, placing the second gear member 582 into and out of engagement with the first gear member 581.

Figure 14:
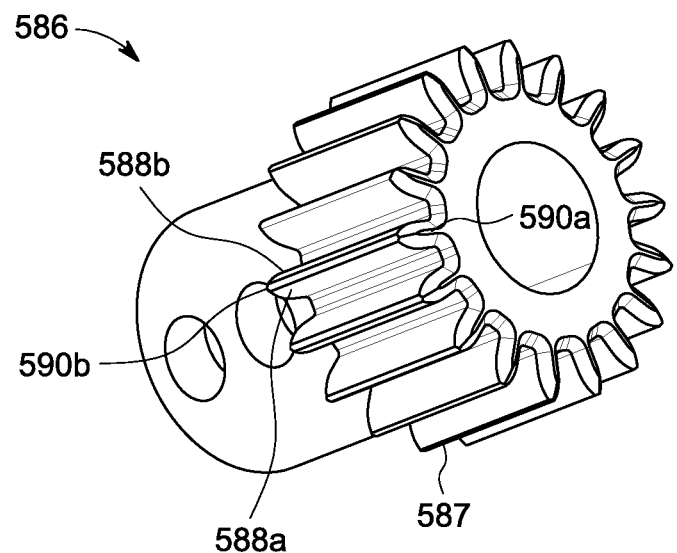
FIG. 14 is a perspective view of an exemplary gear member according to embodiments of the disclosure.

FIG. 14 schematically shows an exemplary gear member 586 which can be used in the gear assembly 580 according to embodiments of the disclosure. As shown, the gear member 586 includes a plurality of teeth 587 each of which has two opposing side surfaces 588a, 588b extending between two end surfaces 590a, 590b. The side surfaces 588a, 588b of the teeth may be generally in parallel with the axis of the gear member 586 configured to engage with the teeth of the mating gear member. At least at one end of the gear member 586 or preferably at both ends of gear member 586, the end surfaces 590a, 590b of the teeth 587 are beveled or chamfered. The surface between adjacent teeth at the end surfaces may also be beveled. The beveled or lofted cut feature along the end or ends of the teeth of the gear members allow the gears to smoothly displace from one another and mesh back up to have a seamless transition when the user operates the switch 610.

Referring to FIGS. 1 and 2, the switch assembly 610 allows the user to operate the instrument 500 smoothly and seamlessly via an intuitive interface. By way of example, the user may place the switch assembly 610 in a first position e.g. an "expansion mode" position provided in the switch guide 556 (FIG. 9) to allow the second gear 582 and first gear 581 engaged, to a second position e.g. a "lordosis mode" position to allow the second gear 512 and first gear 510 disengaged, or to a third position e.g. a "lock mode" position to allow the second gear member 512 to engage both the first gear member 510 and a gear lock 592.

Figure 15:
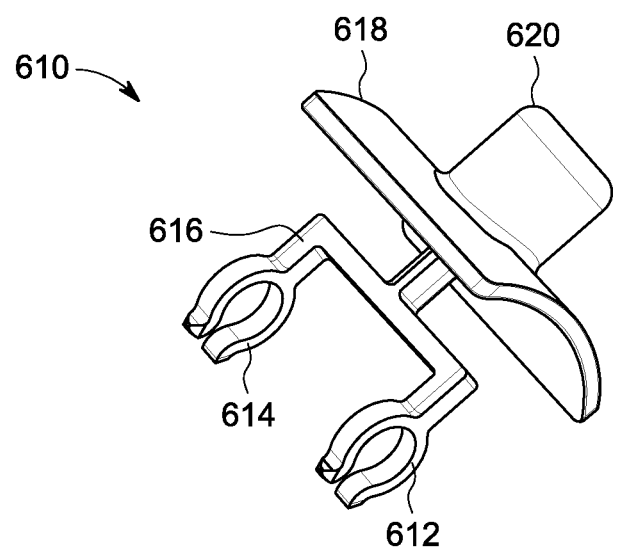
FIG. 15 is a perspective view of an exemplary toggle switch according to embodiments of the disclosure.

FIG. 15 schematically shows a toggle switch 610 which can be used in the operating instrument 500 according to embodiments of the disclosure. As shown, the toggle switch 610 may include a first ring structure 612 and a second ring structure 614 spaced apart e.g. by a generally U-shaped structure 616, which may be coupled to a shield member 618 having a switch nob 620. The first and second ring structures 612, 614 may each have an open end. During assembling, the toggle switch 610 can be snapped on the second drive shaft 512 through the open ends or allowed to slide on from the top of the drive shaft 512 through the top opening of the housing 540. The toggle switch 610 may retain the second gear member 582 between the first and second ring structures 612, 614 and slidably move the second gear member 582 on the second drive shaft 512. The snap on feature allows the toggle switch 610 to be easily attached to or dis-attached from the assembly, enabling more affective cleaning and sterilization of the instrument and reuse for another surgery. The shield 618 on the toggle switch 610 may more effectively prevent bio-materials from passing through the toggle switch into the inner part of the operating instrument.

FIGS. 16-18 illustrate with greater clarity the operation of the switch assembly 610 and the gear assembly 580. In FIG. 16, the toggle switch 610 is placed in a first or "expansion mode" position, which allows the second gear member 582 to engage with the first gear member 510, thereby operably coupling the second drive shaft 512 with the first drive shaft 510. When the second drive shaft 512 is operably coupled with the first drive shaft 510, a rotation of the first drive shaft 510 by the handle 502 causes a rotation of the second drive shaft 512, providing a first operating mode wherein e.g. an expandable spinal implant device can be expanded or contracted. In FIG. 17, the toggle switch 610 is placed in a second or "lordosis mode" position, which allows the second gear member 582 to disengage from the first gear member 581, thereby decoupling the second drive shaft 512 from the first drive shaft 510. When the second drive shaft 512 is decoupled from the first drive shaft 510, the handle 502 rotates solely the first drive shaft 510 whereas the second driving shaft 512 becomes inactive, providing a second operating mode wherein e.g. a spinal implant device can be tilted or lordotically adjusted. In FIG. 18, the toggle switch 610 is placed in a third or "lock mode" position, which allows the second gear member 582 to engage with both the first gear member 581 and the gear lock 592. Because the second gear member 582 is engaged with the gear lock 592, rotation of the second gear member 582 is restricted and as a result, rotation of the first gear member 581 is also restricted due to the engagement with the second gear member 582. When the switch 610 is placed in the third or "lock mode" position, the instrument 500 is locked wherein rotation of the first and second driving shafts 510, 512 is prohibited.

Figure 19:
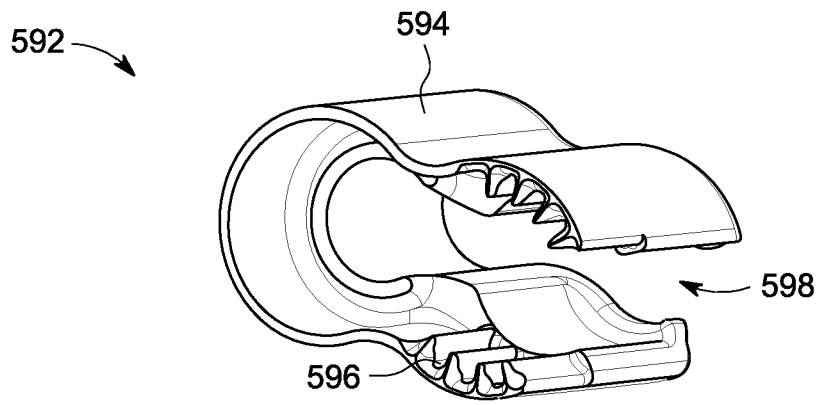
FIG. 19 is a perspective view of an exemplary gear lock according to embodiments of the disclosure.

FIG. 19 is a perspective view of an exemplary gear lock 592 according to embodiments of the disclosure. As shown, the gear lock 592 may include a tubular member 594 having an internal contour such as channels or slots that can accommodate the first and second gear members 581, 582. On the side receiving the second gear member 582, the internal surface of the gear lock 592 may be provided with a teeth configuration 596 configured to mate with the teeth of the second gear member 582. The side of the gear lock 592 may be opened to allow the toggle switch 610 to slidably place or displace the second gear member 582, allowing the teeth on the second gear member 582 to engage or disengage with the teeth 596 on the gear lock 592. The opening 598 may also allow gear lock 592 to flex when being placed inside the partial housing 565 of chassis 560. The outer surface of the gear lock 592 may have a contour configured to mate with the contour of the inner surface of the chassis arms 564 so that the gear lock 592 may fit in or mate with the chassis arms 564 and would not turn when torque applies.

Referring to FIGS. 1-2, the bearing lock assembly 630 operates to lock or unlock the drive shafts 510, 512 and sleeves 520, 522 to or from the chassis 560 in the housing 540. The bearing lock assembly 630 is designed such that when the bearing lock assembly 630 is in a lock mode, the drive shafts 510, 512 and sleeves 520, 522 cannot freely move in the axial direction but may still freely rotate or spin. When the bearing lock assembly 630 is in an unlock mode, the sleeves 520, 522 and drive shafts 510, 512 may slide out of the housing 540 whereas components of the bearing lock assembly 630 may remain in the housing 540. An exemplary bearing lock assembly 630 may include bearings 632, 634, 642, 644, fasteners 633, and retaining plates 652, 654 (FIG. 20).

Figure 20:
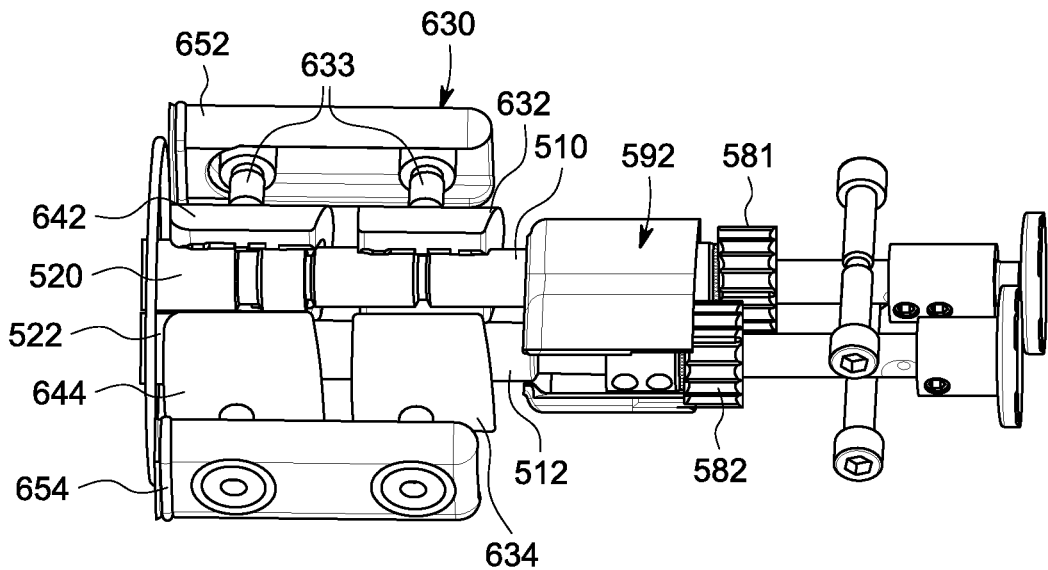
FIG. 20 is a partial perspective view showing a bearing lock assembly and other components of an exemplary surgical operating instrument according to embodiments of the disclosure.
Figure 21:
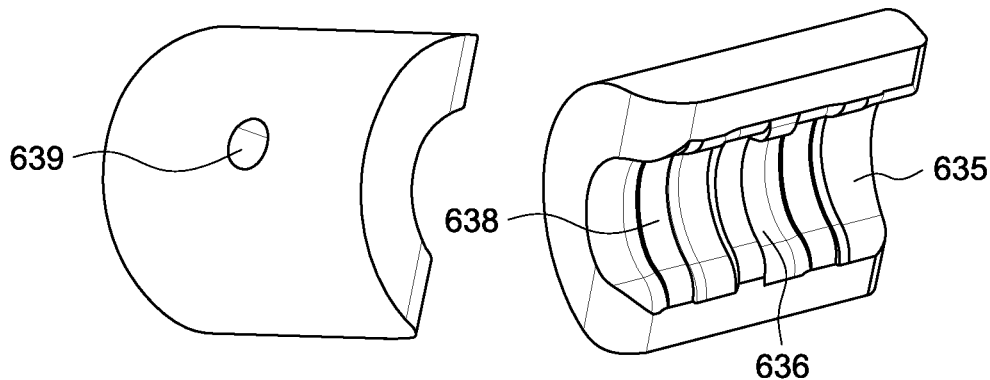
FIG. 21 schematically shows a bearing member which can be used as a drive shaft bearing or sleeve bearing according to embodiments of the disclosure.

FIG. 20 is a partial perspective view showing an exemplary bearing lock assembly 630 and other components of the instrument 500 according to embodiments of the disclosure. In FIG. 20, the housing 540 and chassis 560 are removed to show the bearing lock assembly 630 with greater clarity in relationship to other components of the instrument. As shown, the bearing lock assembly 630 may include a pair of drive shaft bearings 632, 634 configured to lock the drive shafts 510, 512 to the chassis 560 respectively or unlock the drive shafts 510, 512 from the chassis 560. By way of example, the drive shaft bearings 632, 634 may be in the form of a curved plate having a generally arcuate inner surface 635 (FIG. 21). The drive shaft bearings 632, 634 may each be configured to be flush with the chassis main body 562 when assembled and tightened, forming a pair of passages between the pair of drive shaft bearings 632, 634 and the chassis main body 562 to allow the pair of drive shafts 510, 512 to fit in. The drive shaft bearings 632, 634 may each include a notch 636 on the inner surface 635 (FIG. 21) configured to fit into the grooves in each of the pair of drive shafts 510, 512. The notches 636 on the drive shaft bearings 632, 634 prevent the drive shafts 510, 512 from sliding out the housing 540 while allowing them to freely rotate or spin when the bearing lock assembly 630 is the lock mode. The drive shaft bearings 632, 634 may each include one or more ridges 638 on the inner surface 635. When the bearing lock assembly 630 is in the lock mode, the ridges 638 on the inner surface of the drive shaft bearings 632, 634 and the ridges 569 on the inner surface of the chassis 560 press against the drive shafts 510, 512, preventing the drive shafts 510, 512 from freely moving in the axial direction.

The drive shaft bearings 632, 634 may each be provided with a hole 639 having an internal thread. The fasteners 633, which can be in the form of shoulder bolts or the like, may have an external thread to be received in the hole 639 of the drive shaft bearings 632, 634. When torqued, the fasteners 633 may turn in the threaded holes 639, pushing the drive shaft bearings 632, 634 against the chassis 560, thereby tightening the drive shafts 510, 512 to the chassis 560. Turning the fasteners 633 in an opposite direction would loosen the drive shaft bearings 632, 634, thereby unlocking the drive shafts 510, 512 from the chassis 560.

The bearing lock assembly 630 may include a pair of sleeve bearings 642, 644 configured to lock sleeves 520, 522 to the chassis 560 respectively or unlock the sleeve 520, 522 from the chassis 560. Similar to the drive shaft bearings 632, 634, the sleeve bearings 642, 644 may be in the form of a curved plate having a generally arcuate inner surface 635. The sleeve bearings 642, 644 may each be configured to be flush with the chassis main body 562 when assembled and tightened, forming a pair of passages between the pair of sleeve bearings 642, 644 and the chassis main body 562 to allow the pair of sleeves 520, 522 to fit in.

The sleeve bearings 642, 644 may each include a notch 636 on the inner surface 635 configured to fit into the grooves in each of the pair of sleeves 520, 522. The notches 636 on the sleeve bearings 642, 644 prevent the sleeves 520, 522 from sliding out the housing 540 while allowing them to spin when the bearing lock assembly 630 is in a lock mode. In some embodiments, the grooves 520d, 522d in the sleeves 520, 522 may be machined slightly wider than the notch on the sleeve bearing 642, 644 to allow slight axial movement of the sleeves 520, 522, which may be needed when the operating instrument 500 is connected with e.g. an interbody fusion device. The sleeve bearings 642, 644 may also include one or more ridges on the internal surface. When the bearing lock assembly 630 is in the lock mode, the ridges 638 on the inner surface of the sleeve bearings 642, 644 and the ridges 569 on the inner surface of the chassis 560 press against the sleeves 520, 522, preventing the sleeves 520, 522 from freely moving in the axial direction. This dynamic lock system allows for ease of assembly and disassembly for cleaning and sterilization activities so that the instrument 500 may be reused for multiple surgeries while providing a strong assembly connection during operation.

The sleeve bearings 642, 644, similar to the drive shaft bearings 632, 634, may be provided with a hole 639 having an internal thread for connection with a fastener 633. The fasteners 633, which can be a shoulder bolt or the like, may have an external thread to be received in the hole of the sleeve bearings. When torqued, the fasteners 633 may turn in the threaded hole, pushing the sleeve bearings to flush with the chassis 560. Turning the fasteners in an opposite direction would loosen the sleeve bearings 642, 644 from the chassis 560, unlocking the sleeves 520, 522.

Figure 22:
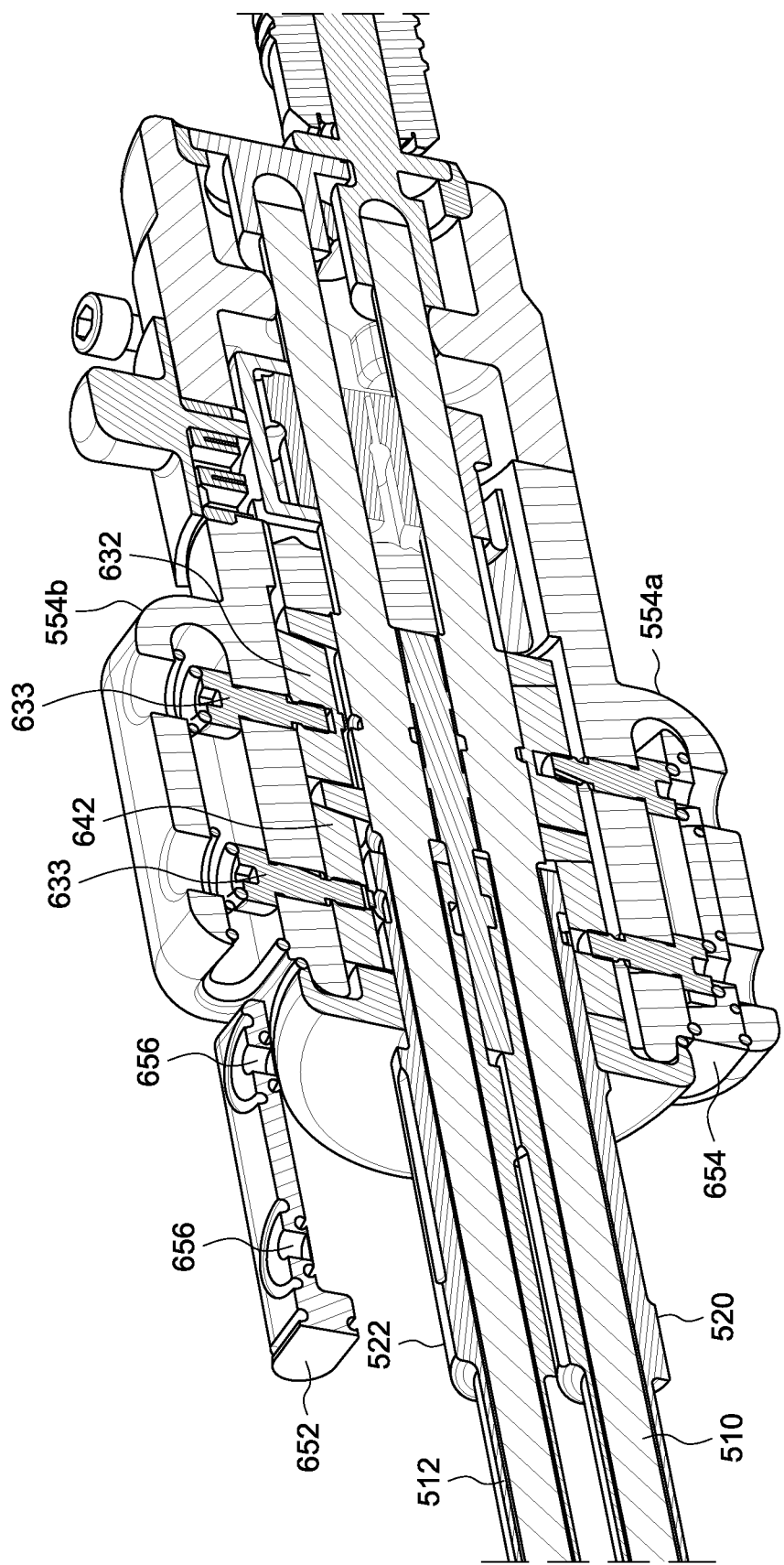
FIG. 22 is a partial, cutaway view of an exemplary surgical operating instrument showing a bearing lock assembly including retaining plates and other components according to embodiments of the disclosure.

The bearing lock assembly 630 may include a pair of retaining plates 652, 654 for retaining the fasteners 633 within the housing. The retaining plates 652, 654 include apertures 656 allowing a torque applying tool to access the fasteners 633 in tightening or loosening the bearings (FIG. 22). However, the retaining plates 652, 654 restrict the fasteners 633 from moving outwardly or in an axial direction of the fasteners, thereby preventing the fasteners 633 from coming loose from the entire assembly after being torqued in loosening the bearings. The retaining plates 652, 654 allow the sleeves 520, 522 and drive shafts 510, 512 to be taken out from the assembly for cleaning, sterilization, or replacement without having to take the fasteners 633 all the way out of the assembly. This provides more ease for hospital personnel when they need to disassemble for replacement, cleaning, and sterilization. The retaining plates may contain O-rings of a medical grade silicone to assure that biomaterial or water not make its way into the crevices of the bearing lock assembly.

The retaining plates 652, 654 may be configured to snap into the sub-housings 554a, 554b through a press fit or other suitable means (FIG. 22). Grooves may be provided in the areas adjacent to the apertures 656 for sealing gaskets, O-rings, or of the like, thus preventing water, debris or biomaterials from entering into the housing via the apertures. When needed, the retaining plates 652, 654 may be easily taken out for further cleaning and sterilization. FIG. 22 is a partial, cutaway view of the operating instrument showing the retaining plates 652, 654 which can be snapped in and taken out of the sub-housings 554a, 554b.

Returning to FIGS. 1-2, the operating instrument 500 may include a first dial 506 and a second dial 508 configured to provide the user with information about operation of the instrument. The first dial 506 may be coupled to the first drive shaft 510. The second dial 508 may be coupled to the second drive shaft 512. By way of example, the first dial 506 may be provided with an aperture configured to allow the first drive shaft 510 or the adapter 504 to fit in. The second dial 508 may be provided with a channel configured to receive or couple with the second drive shaft 512.

In use, the first dial 506 rotates with the first drive shaft 510 and the indicia on the first dial 506 provide the user with information about revolution(s) of first drive shaft 510. The second dial 508 rotates with the second drive shaft 512 and the indicia on the second dial 508 provide the user with information about revolution(s) of the second drive shaft 512. As described above, when the second drive shaft 512 is coupled with the first drive shaft 510 by the gear assembly 580, the handle 502 rotates both the first and second driving shafts 510, 512, and as such, both the first dial 506 and second dial 508 revolve, providing an indication to the user of the first operating mode of the instrument 500 or an indication of the level of height expansion. When the second drive shaft 512 is decoupled from the first drive shaft 510 by the gear assembly 580, the handle 502 rotates solely the first drive shaft 510, and as such, only the first dial 506 coupled to the first drive shaft 510 revolves, providing an indication to the user of a second operating mode of the instrument 500. The indication of the first dial and second dial when decoupled equates to an added angle of lordosis or kyphosis when the first drive shaft is driven unequally with the second drive shaft.

In embodiments of the disclosure, the instrument 500 operates an interbody infusion implant device in surgical procedures and the indicia provided on the first and second dials 506, 508 may be configured to allow the user to measure the amount of expansion, contraction, and/or lordosis adjustment added to the intervertebral disc space of the patient. For example, indicia may be provided on the first dial 506 to indicate or allow the user to measure added lordosis. By way of example, four (4) degrees may be an equivalent to one full turn of the dial 506 or two (2) degrees equivalent to a half turn of the dial 506. Indicia may also be provided on the first and/or second dials 506, 508 to indicate or allow the user to measure the added height or expansion. By way of example, 2.2 mm may be an equivalent to one full turn of the first and second dials 506, 508 or 1.1 mm equivalent to a half turn of the dials 506, 508.

Referring to FIGS. 1-2, in use the instrument 500 may be connected with a workpiece such as a spinal implant device via sleeves 520, 522. The user may spin or rotate the sleeves 520, 522, for example, inwards to thread the instrument 500 onto the implant device. Before connecting with an implant device, the user may first set the instrument 500 in the lock mode e.g. by placing the switch 610 in the middle position in the switch guide (FIG. 18) so that the first and second gear members are locked and rotation of the drive shafts 510, 512 is prohibited. In placing the implant device into the patient's vertebral space, a forward force may be needed in some situations. When needed, the handle 502 of the instrument 500 may be temporarily removed and replaced with the impact cap 503 or slap hammer 670. A forward force may be then exerted through the instrument 500 by striking the impact cap 503 using e.g. a mallet. Once the implant device is properly positioned in the patient's vertebral space, the impact cap 503 may be removed and replaced with the handle 502 for operation of the implant device. In some embodiments, the handle 502 or impact cap 503 may be removed and a slap hammer 670 can be connected to the instrument e.g. to the adapter 504 or the top of the housing 540. The slap hammer 670 acts as an attachment to provide a removal or pull force to the implant if the surgeon needs to remove the implant back out of the disc space after insertion.

To achieve expansion of the implant device, the user may place the switch 610 to the proximal position, allowing the first and second gear members to be free from the locked position and engaged to couple the first and second drive shafts 510, 512. The user may then rotate the handle 502 in a direction e.g. clockwise to apply torque to the first drive shaft 502. The rotation of the first drive shaft 512 simultaneously causes rotation of the second drive shaft 51, thereby effecting expansion of the implant device in fine increments. If desired the user may rotate the handle 502 in an opposite direction e.g. counterclockwise, to contract or finely adjust the expansion level of the implant device. The gear assembly 580 may be configured such that a rotation of the first drive shaft 510 in a first direction, e.g. clockwise, causes a rotation of the second drive shaft 512 in a second direction opposite to the first direction, e.g. counterclockwise. Alternatively, the gear assembly 580 may be configured such that rotating the handle 502 causes the first and second drive shafts 510, 512 to rotate in the same direction.

To achieve lordosis, the user may place the switch 610 to the distal position, allowing the first and second gear members to be disengaged thereby decoupling the second drive shaft 512 from the first drive shaft 510. The user may then rotate the handle 502 in a direction e.g. clockwise, applying torque solely to the first drive shaft 510 since the second drive shaft 512 becomes inactive. The rotation of only the first drive shaft 510 causes the implant device to tilt, thereby achieving lordosis. If desired, the user may rotate the handle 502 in an opposite direction, e.g. counterclockwise, to adjust or remove the levels of the lordosis while keeping the first drive shaft 510 and second drive shaft 512 constrained from rotation. This constraint assures that the drive shafts are unable to contract the implant back down while the instrument is being disconnected from the implant.

To disconnect the operating instrument 500 from the implant device, the user may place the switch 610 to the middle position to set the instrument in a lock mode and then spin the sleeves 520, 522 e.g. outwards to unthread the instrument 500 from the implant device.

Various embodiments of an operating instrument have been described. It is to be understood that the disclosure is not limited to the particular embodiments described. An aspect described in conjunction with a particular embodiment is not necessarily limited to that embodiment and can be practiced in any other embodiments.

Various embodiments are described with reference to the figures. It should be noted that some figures are not necessarily drawn to scale. The figures are only intended to facilitate the description of specific embodiments and are not intended as an exhaustive description or as a limitation on the scope of the disclosure. Further, in the figures and description, specific details may be set forth in order to provide a thorough understanding of the disclosure. It will be apparent to one of ordinary skill in the art that some of these specific details may not be employed to practice embodiments of the disclosure. In other instances, well known components may not be shown or described in detail in order to avoid unnecessarily obscuring embodiments of the disclosure.

All technical and scientific terms used herein have the meaning as commonly understood by one of ordinary skill in the art unless specifically defined otherwise. As used in the description and appended claims, the singular forms of "a," "an," and "the" include plural references unless the context clearly dictates otherwise. The term "or" refers to a nonexclusive "or" unless the context clearly dictates otherwise.

Those skilled in the art will appreciate that various other modifications may be made. All these or other variations and modifications are contemplated by the inventors and within the scope of the invention.

The invention claimed is:

1. An operating instrument, comprising:
   a housing;
   a chassis;
   a first drive shaft and a second drive shaft each having a first portion supported by the chassis in the housing and a second portion extending out of the housing;
   a gear assembly comprising a first gear member fixedly received on the first portion of the first drive shaft and a second gear member slidably received on the first portion of the second drive shaft;
   a switch assembly operable to place the second gear member into engagement with the first gear member thereby coupling the second drive shaft with the first drive shaft to provide a first operating mode wherein the second drive shaft is rotatable with the first drive shaft, or displace the second gear member out of engagement with the first gear member thereby decoupling the second drive shaft from the first drive shaft to provide a second operating mode wherein the second drive shaft is non-rotatable with the first drive shaft; and
   a bearing lock assembly operable to lock the first and second drive shafts to the chassis whereby the first and second drive shafts are restricted from sliding out of the housing and are capable of freely rotating, or unlock the first and second drive shafts from the chassis to allow the first and second drive shafts to slide out of the housing.

2. The operating instrument of claim 1, further comprising a handle connectable to the first drive shaft for applying torque.

3. The operating instrument of claim 1, further comprising an impact cap configured to place on the housing for receiving a striking force.

4. The operating instrument of claim 1, further comprising a slap hammer connectable to the operating instrument for applying a pull force to the operating instrument.

5. The operating instrument of claim 1, further comprising a gear lock disposed in the chassis, wherein the switch assembly is further operable to place the second gear member into engagement with both the gear lock and the first gear member thereby providing a third operating mode wherein a rotation of the second and first drive shafts is restricted.

6. The operating instrument of claim 5, wherein the switch assembly comprises a pair of open-ring structures that snap or slide on the second drive shaft placing the second gear member in between the pair of the open-ring structures.

7. The operating instrument of claim 6, wherein the switch assembly further comprises a shield member configured to prevent debris or biomaterials from entering into the housing.

8. The operating instrument of claim 1, wherein each of the first and second gear members comprises a plurality of teeth each having two end surfaces and two side surfaces extending between the two end surfaces, wherein the two end surfaces are beveled to allow smooth engagement or disengagement of the first and second gear members.

9. The operating instrument of claim 8, wherein the gear assembly is configured such that in the first operating mode a rotation of the first drive shaft in a first direction causes a rotation of the second drive shaft in a second direction opposite to the first direction.

10. The operating instrument of claim 1, wherein the chassis comprises a first portion including a main body supporting the first and second drive shafts, and a second portion including spaced-apart arms defining a partial housing for the gear assembly and the switch assembly, wherein the main body is provided with a pair of elongate channels along opposite sides of the main body configured to receive the first and second drive shafts.

11. The operating instrument of claim 10, wherein the main body of the chassis further comprises a base at an end of the main body provided with a pair of openings, allowing the first and second drive shafts to pass through the pair of openings in the base, be received in the pair of elongate channels, and enter into the partial housing defined by the spaced apart arms.

12. The operating instrument of claim 11, wherein the main body of the chassis further comprises a divider dividing elongate channels into two sections, the divider is provided with a pair of openings aligned with the pair of openings in the base of the main body.

13. The operating instrument of claim 12 wherein the chassis is constructed of stainless steel or aluminum.

14. The operating instrument of claim 12 wherein the bearing lock assembly comprises a pair of bearings configured to lock or fix the first and second drive shafts to the main body of the chassis.

15. The operating instrument of claim 14, wherein the pair of bearings comprises a circumferential notch on an internal surface of the each of the pair of bearings configured to mate with a groove provided in each of the first and second drive shafts to restrict the first and second drive shafts from sliding out of the housing when locked or fixed.

16. The operating instrument of claim 15, wherein each of the first and second pairs of the bearings further comprises one or more circumferential ridges on the internal surface of the pairs of the bearings, the main body of the chassis further comprises a plurality of ridges on an internal surface of each of the pair of elongate channels, wherein the ridges of the pair of bearings and of the main body of the chassis are configured to restrict free axial movement of the first and second drive shafts when locked or fixed.

17. The operating instrument of claim 12, wherein the bearing lock assembly further comprises:
a first pair of fasteners configured to drive the pair of bearings, wherein a rotation of the pair of fasteners allows the pair of bearings to tighten or loosen the first and second drive shafts in the pair of elongate channels of the chassis, and
a pair of retaining plates coupled to the housing configured to restrict axial movement of the pair of fasteners.

18. The operating instrument of claim 1, wherein the housing comprises a first end portion enclosing at least the gear assembly and a second end portion enclosing at least the bearing lock assembly, wherein the first end portion of the housing comprises a pair of housing covers removably attached to the chassis, each of the pair of housing covers comprises a shoulder configured to support an impact cap.

19. The operating instrument of claim 18, wherein the housing comprises a guide track providing guidance in operating the switch assembly in at least the first and second operating modes, and indicia indicating at least the first and second operating modes.

20. The operating instrument of claim 19, further comprising a guide gasket constructed of silicone configured to smooth the operating of the switch assembly in guide track, to help ensure the switch assembly stay fixed in a selected operating mode, and/or prevent debris or biomaterials from entering the housing.

* * * * *